(12) United States Patent
Smith et al.

(10) Patent No.: US 11,135,394 B2
(45) Date of Patent: Oct. 5, 2021

(54) HUMIDIFIER AND/OR FLOW GENERATOR FOR CPAP DEVICE

(71) Applicant: ResMed Pty Ltd, Bella Vista (AU)

(72) Inventors: Ian Malcolm Smith, Sydney (AU);
John Michael Snow, Sydney (AU);
Perry David Lithgow, Sydney (AU);
Dan Kao, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 421 days.

(21) Appl. No.: 16/156,049

(22) Filed: Oct. 10, 2018

(65) Prior Publication Data
US 2019/0038865 A1    Feb. 7, 2019

Related U.S. Application Data

(63) Continuation of application No. 14/687,223, filed on Apr. 15, 2015, now Pat. No. 10,124,143, which is a
(Continued)

(51) Int. Cl.
*A61M 16/16* (2006.01)
*A61M 16/10* (2006.01)
(Continued)

(52) U.S. Cl.
CPC ........ *A61M 16/16* (2013.01); *A61M 16/0057* (2013.01); *A61M 16/0066* (2013.01);
(Continued)

(58) Field of Classification Search
CPC ........ A41D 13/0055; A61F 2007/0063; A61G 10/04; A61M 2205/3606; B01D 5/0039;
(Continued)

(56) References Cited

U.S. PATENT DOCUMENTS

| 707,301 A | 8/1902 | Chesterman |
| 1,475,289 A | 11/1923 | Diescher |
| (Continued) | | |

FOREIGN PATENT DOCUMENTS

| CA | 2 890 591 | 4/2004 |
| CN | 1314192 | 9/2001 |
| (Continued) | | |

OTHER PUBLICATIONS

Extended European Search Report dated Mar. 28, 2018 issued in European Application No. 17193255.1 (7 pages).
(Continued)

*Primary Examiner* — Annette Dixon
(74) *Attorney, Agent, or Firm* — Nixon & Vanderhye P.C.

(57) ABSTRACT

A flow generator for a CPAP system configured to deliver a pressurized flow of respiratory gas to a patient's airways includes a housing and a motorized fan positioned within the housing. The motorized fan is configured to pressurize the flow of respiratory gas. In addition, an outlet port is provided in the housing. The outlet port is configured to connect to a humidifier or an air delivery tube and is in communication with an outlet of the motorized fan. The flow generator further includes a water collection receptacle in communication with the outlet port and the motorized fan outlet. The water collection receptacle is configured to collect water entering the flow generator through the outlet port before the water reaches the motorized fan outlet.

23 Claims, 20 Drawing Sheets

Related U.S. Application Data continuation of application No. 11/988,870, filed as application No. PCT/AU2006/001170 on Aug. 15, 2006, now Pat. No. 9,038,629.

(60) Provisional application No. 60/707,948, filed on Aug. 15, 2005.

(51) Int. Cl.
| | |
|---|---|
| *A61M 16/08* | (2006.01) |
| *A61M 16/00* | (2006.01) |
| *A61M 16/06* | (2006.01) |
| *B01D 47/02* | (2006.01) |

(52) U.S. Cl.
CPC .... *A61M 16/0075* (2013.01); *A61M 16/0616* (2014.02); *A61M 16/0666* (2013.01); *A61M 16/08* (2013.01); *A61M 16/0816* (2013.01); *A61M 16/0875* (2013.01); *A61M 16/10* (2013.01); *A61M 16/109* (2014.02); *A61M 16/1075* (2013.01); *A61M 2205/02* (2013.01); *A61M 2205/3334* (2013.01); *A61M 2205/42* (2013.01); *A61M 2209/086* (2013.01); *B01D 47/02* (2013.01)

(58) Field of Classification Search
CPC ........ F24F 1/04; F24F 2221/12; F24F 3/1405; F24F 5/0017; F25D 2400/26; F25D 3/08; Y02A 20/00; Y02A 20/109; Y02E 60/14; Y02E 60/147
See application file for complete search history.

(56) References Cited

U.S. PATENT DOCUMENTS

| | | | |
|---|---|---|---|
| 2,500,404 A | 3/1950 | Donnelly | |
| 2,702,546 A * | 2/1955 | Gilroy | A61G 10/04 128/204.16 |
| 2,872,560 A | 2/1959 | Bowles | |
| 2,998,198 A | 8/1961 | Young | |
| 3,090,380 A | 5/1963 | Dold | |
| 3,275,344 A | 9/1966 | Kendt | |
| 3,388,705 A | 6/1968 | Grosshandler | |
| 3,680,896 A | 8/1972 | Cupit | |
| 4,000,341 A | 12/1976 | Matson | |
| 4,028,444 A | 6/1977 | Brown et al. | |
| 4,049,233 A | 9/1977 | Brandin | |
| 4,124,046 A | 11/1978 | Lundberg | |
| 4,164,645 A | 8/1979 | Dogliotti | |
| 4,165,456 A | 8/1979 | Dogliotti | |
| 4,201,737 A | 5/1980 | Carden | |
| 4,203,027 A | 5/1980 | O'Hare et al. | |
| 4,268,815 A | 9/1981 | Clark | |
| 4,399,080 A | 8/1983 | Swank | |
| 4,496,132 A | 1/1985 | Winegarten | |
| 4,557,261 A | 12/1985 | Rügheimer | |
| 4,575,128 A | 3/1986 | Sundquist | |
| 4,715,998 A | 12/1987 | Clow | |
| 4,921,642 A | 5/1990 | Latorraca | |
| 4,953,897 A | 9/1990 | Klober | |
| 5,301,516 A * | 4/1994 | Poindexter | F24F 3/1405 62/126 |
| 5,329,939 A | 7/1994 | Howe | |
| 5,349,946 A | 9/1994 | McComb | |
| 5,439,448 A | 8/1995 | Leschinsky et al. | |
| 5,564,415 A | 10/1996 | Dobson et al. | |
| 5,673,687 A | 10/1997 | Dobson et al. | |
| 5,943,473 A | 8/1999 | Levine | |
| 6,024,694 A | 2/2000 | Goldberg et al. | |
| 6,170,282 B1 * | 1/2001 | Eddins | F24F 1/04 62/259.3 |
| 6,438,180 B1 | 8/2002 | Kavcic et al. | |
| 6,554,260 B1 | 4/2003 | Lipscombe et al. | |
| 6,648,664 B1 | 11/2003 | McHugh et al. | |
| 6,718,974 B1 | 4/2004 | Moberg | |
| 6,811,546 B1 | 11/2004 | Callas et al. | |
| 6,843,207 B2 | 1/2005 | Kanzaki et al. | |
| 6,935,337 B2 | 8/2005 | Virr et al. | |
| 6,988,497 B2 | 1/2006 | Levine | |
| 7,137,388 B2 | 11/2006 | Virr et al. | |
| D542,900 S | 5/2007 | Snow et al. | |
| 7,327,949 B1 | 2/2008 | Cheng et al. | |
| 7,413,173 B2 | 8/2008 | DiMatteo et al. | |
| 7,614,398 B2 | 11/2009 | Virr et al. | |
| 8,006,691 B2 | 8/2011 | Kenyon et al. | |
| 8,049,143 B2 | 11/2011 | Andel et al. | |
| 8,240,306 B2 | 8/2012 | Cortez et al. | |
| RE44,453 E | 8/2013 | Virr et al. | |
| 8,544,465 B2 | 10/2013 | Smith | |
| 9,038,629 B2 | 5/2015 | Smith et al. | |
| 9,038,631 B2 | 5/2015 | Bath | |
| 9,038,632 B2 | 5/2015 | Crumblin | |
| 9,227,035 B2 | 1/2016 | Crumblin | |
| 9,393,377 B2 | 7/2016 | Smith | |
| 9,539,409 B2 | 1/2017 | Crumblin | |
| 9,895,509 B2 | 2/2018 | Smith | |
| 2002/0195110 A1 | 12/2002 | Watton | |
| 2003/0066526 A1 | 4/2003 | Thudor et al. | |
| 2003/0172931 A1 | 9/2003 | Kerechanin, II et al. | |
| 2004/0011073 A1 * | 1/2004 | Blackstone | A41D 13/0055 62/420 |
| 2004/0055597 A1 | 3/2004 | Virr et al. | |
| 2004/0065335 A1 | 4/2004 | Huber et al. | |
| 2004/0076412 A1 | 4/2004 | Kanzaki et al. | |
| 2004/0221843 A1 | 11/2004 | Baecke | |
| 2004/0226562 A1 | 11/2004 | Bordewick | |
| 2005/0103339 A1 | 5/2005 | Daly et al. | |
| 2005/0178383 A1 | 8/2005 | Mackie et al. | |
| 2006/0130836 A1 | 6/2006 | Wixey et al. | |
| 2006/0237005 A1 | 10/2006 | Virr et al. | |
| 2008/0072900 A1 | 3/2008 | Kenyon et al. | |
| 2008/0302361 A1 | 12/2008 | Snow et al. | |
| 2009/0120434 A1 | 5/2009 | Smith et al. | |
| 2009/0194106 A1 | 8/2009 | Smith et al. | |
| 2010/0154796 A1 | 6/2010 | Smith et al. | |
| 2010/0206308 A1 * | 8/2010 | Klasek | A61M 16/1085 128/203.27 |
| 2011/0271956 A2 | 11/2011 | Smith et al. | |
| 2015/0231358 A1 | 8/2015 | Smith et al. | |
| 2016/0317775 A1 | 11/2016 | Smith | |

FOREIGN PATENT DOCUMENTS

| | | |
|---|---|---|
| EP | 0 339 234 A1 | 11/1989 |
| EP | 1 138 341 | 10/2001 |
| EP | 1 319 880 | 6/2003 |
| EP | 1 520 599 | 4/2005 |
| FR | 2535613 A1 | 5/1984 |
| FR | 2 663 547 | 12/1991 |
| GB | 2 116 434 A | 9/1983 |
| GB | 2 173 107 | 10/1986 |
| GB | 2 173 108 | 10/1986 |
| WO | 99/22793 | 5/1999 |
| WO | WO 02/066107 A1 | 8/2002 |
| WO | 03/066145 | 8/2003 |
| WO | WO 2004/043528 A1 | 5/2004 |
| WO | 2004/108198 A1 | 12/2004 |
| WO | WO 2004/112873 A1 | 12/2004 |
| WO | 2007/019625 | 2/2007 |

OTHER PUBLICATIONS

Extended Search Report dated Feb. 10, 2016 issued in European Application No. 15185116.9 (5 pages).
Notification of the Third Office Action dated Feb. 26, 2016 issued in Chinese Application No. 201310046245.3 with English translation (11 pages).
Office Action dated Dec. 22, 2015 issued in related U.S. Appl. No. 13/974,277 (21 pages).
First Examination Report dated Sep. 7, 2015 issued in New Zealand Application No. 711099 (2 pages).

(56) References Cited

OTHER PUBLICATIONS

Notification of the Second Office Action dated Aug. 14, 2015 issued in Chinese Application No. 201310046245.3 with English translation (12 pages).
First Examination Report dated Mar. 8, 2013 in New Zealand Application No. 607890 (2 pages).
Office Action issued in Chinese Application No. 20068029792.9 dated Dec. 11, 2009.
Notification of the Fifth Office Action dated Jun. 10, 2014 issued in corresponding Chinese Application No. 201110068459.1 (10 pages).
First Communication dated May 9, 2014 in European Application No. 06774815.2 (7 pages).
Further Examination Report dated Feb. 28, 2014 in New Zealand Application No. 607890 (2 pages).
First Examination Report dated Feb. 28, 2014 in New Zealand Application No. 621227 (2 pages).
Chinese Office Action dated Jun. 18, 2013 in Chinese Application No. 201110068459.1 with English translation (9 pages).
Extended European Search Report dated Jul. 3, 2013 in European Application No. 06774815.2 (10 pages).
"lid". Collins English Dictionary, 2000, http://www.credoreference.com/entry/hcengdict/either (Feb. 24, 2014).
Notification of the Fourth Office Action dated Dec. 30, 2013 in Chinese Application No. 201110068459.1, with English translation (10 pages).
International Search Report dated Sep. 18, 2006 in International Application No. PCT/AU2006/001172.
Notification of the Second Office Action mailed in Chinese Application No. 201110068459.1, with English Translation.
Further Examination Report dated Mar. 4, 2013 in New Zealand Application No. 597020 (2 pages).
Notice of Opposition to Grant of Patent filed on Jun. 27, 2011 against New Zealand Application No. 564886.
Examination Report dated Dec. 14, 2011 in New Zealand Appln. No. 586325 (3 pages).
International Search Report dated Nov. 21, 2006.
U.S. Appl. No. 60/707,949, filed Aug. 15, 2005 (p. 6 of specification).
U.S. Appl. No. 60/707,951, filed Aug. 15, 2005 (p. 6 of specification).
New Zealand Exam Report dated Dec. 14, 2011 in New Zealand Appln. No. 597020 (3 pages).
Examiner's First Report dated Mar. 23, 2011 in Australian Application No. 2006281985 (2 pages).
Examination Report dated Jun. 29, 2010 in New Zealand Appln. No. 586325 (2 pages).
Counterstatement filed Oct. 26, 2011 in New Zealand Application No. 564886 (13 pages).
Respironics, Inc., REMStar Heated Humidifier Manual.
Extended European Search Report dated Mar. 10, 2021 issued in European Application No. 20195220.7 (7 pages).

\* cited by examiner

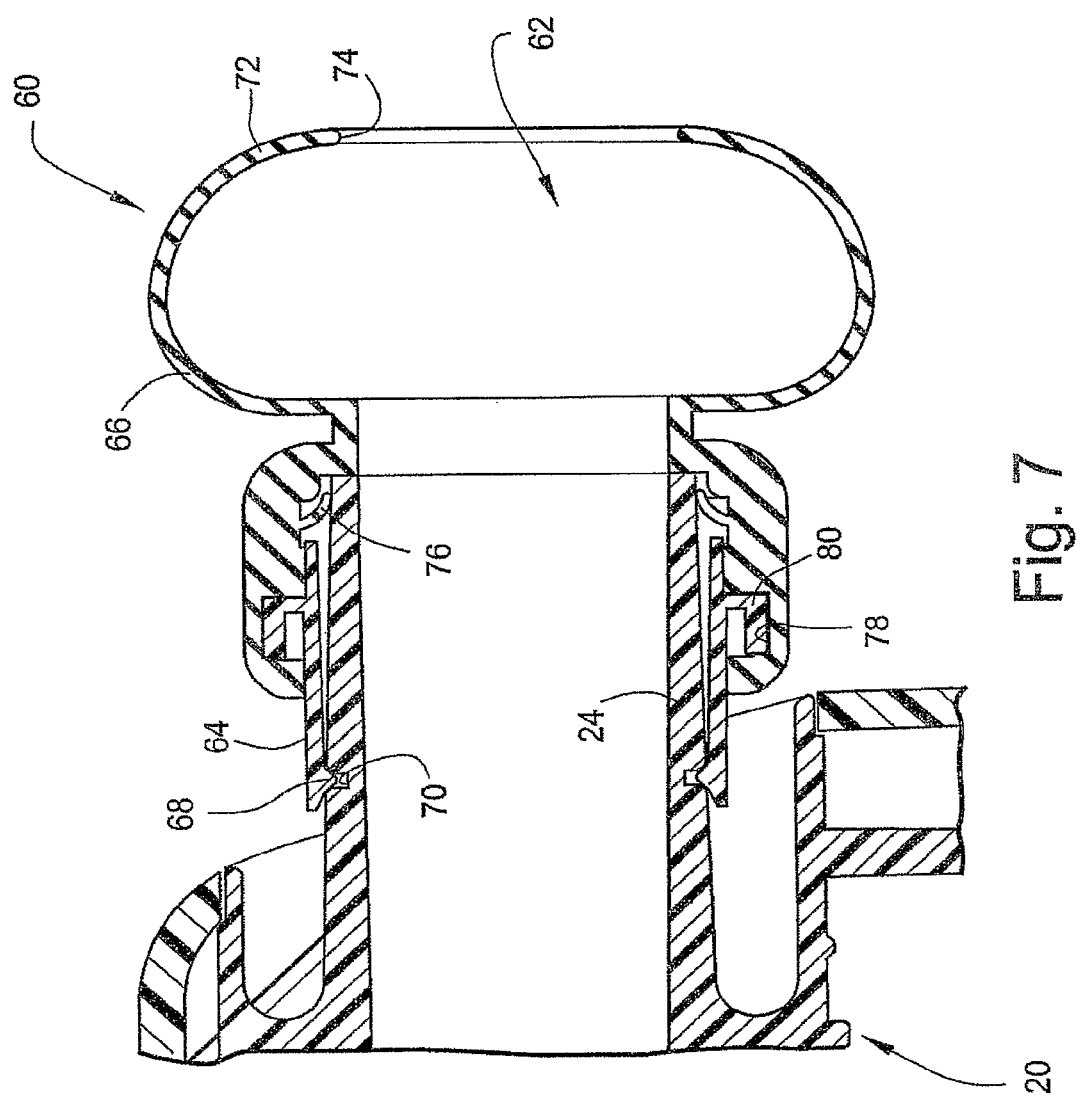

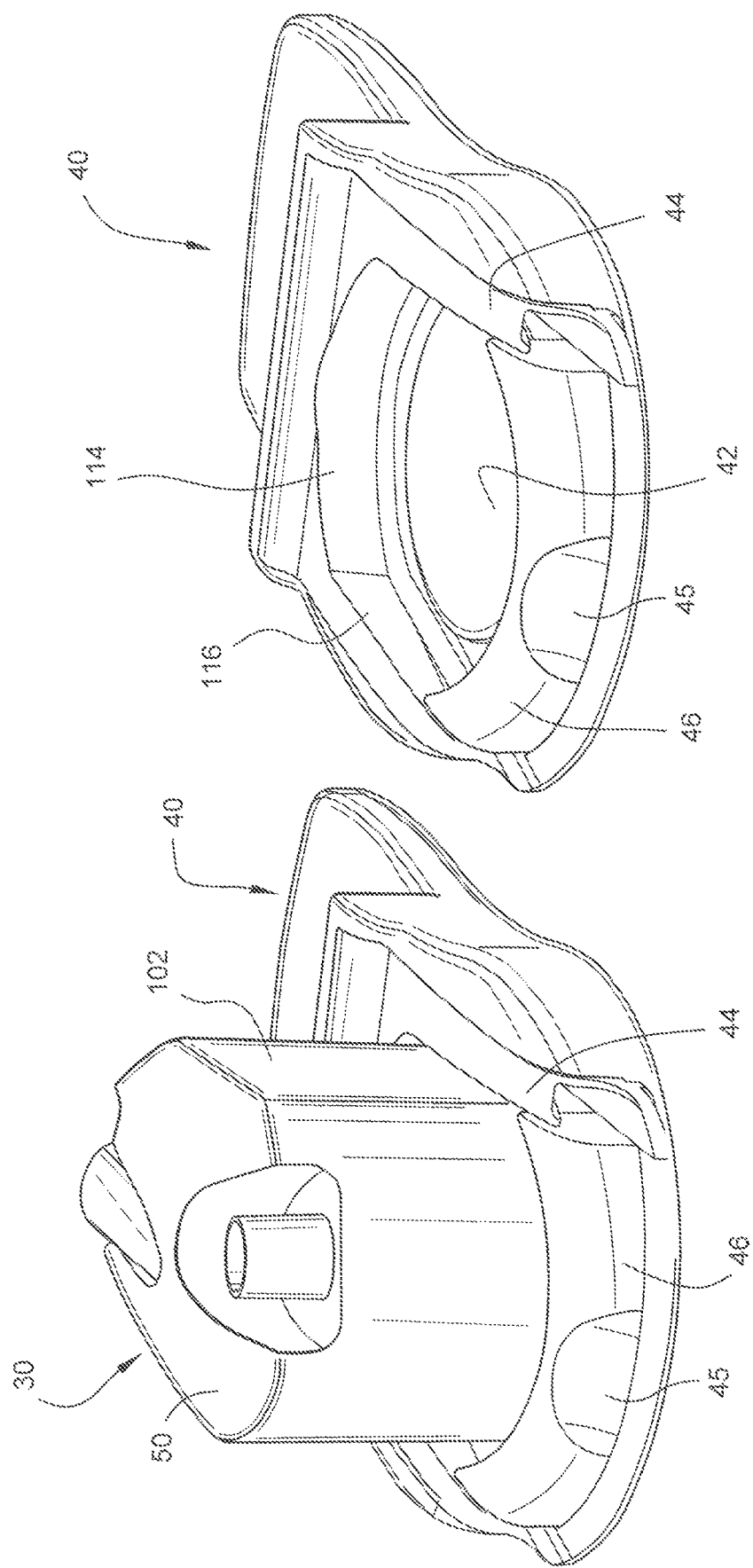

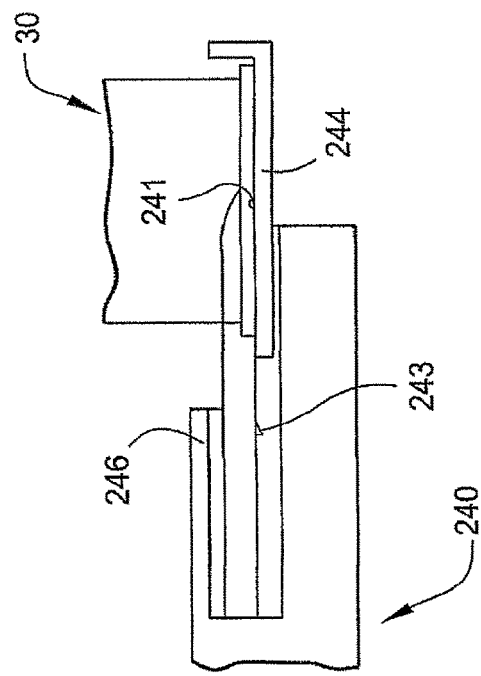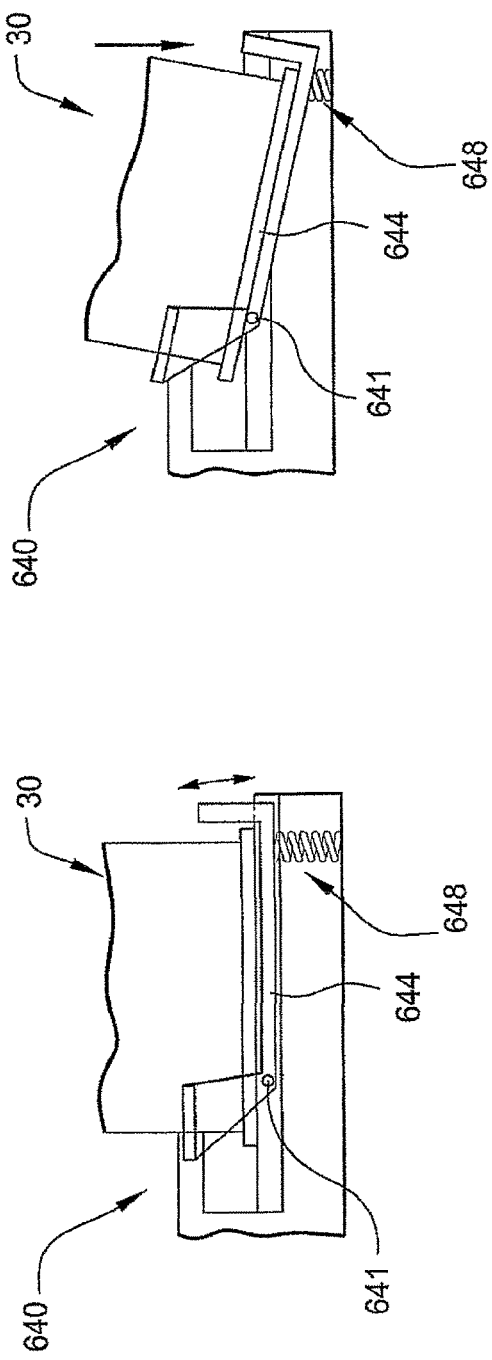

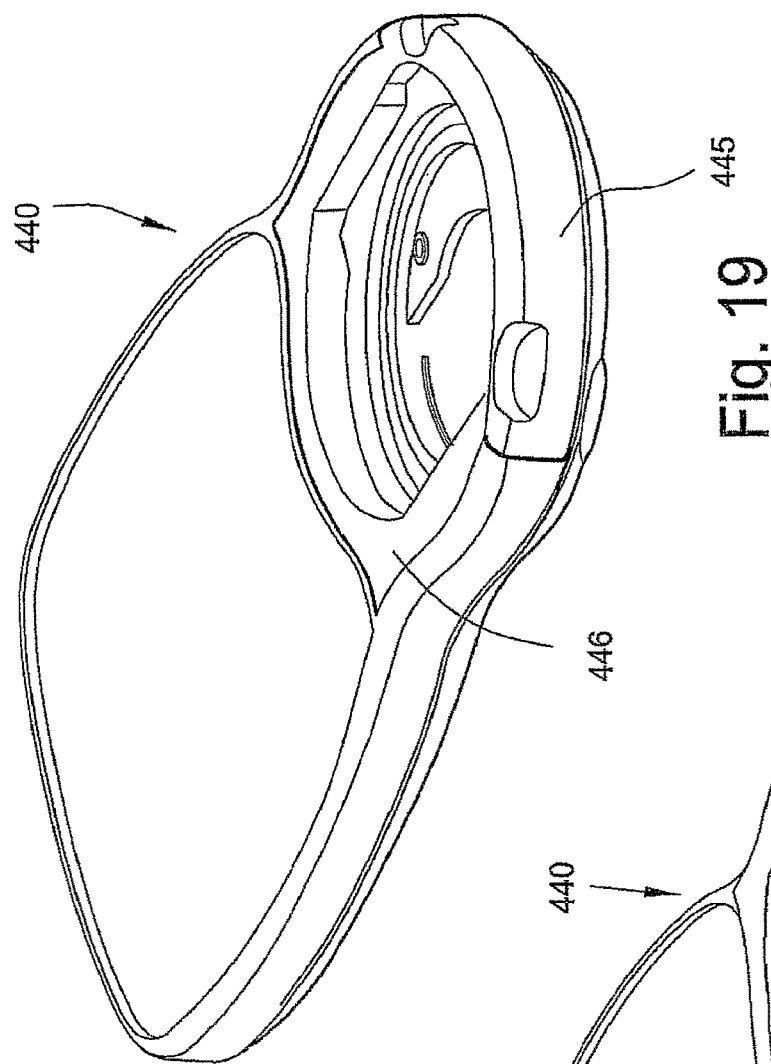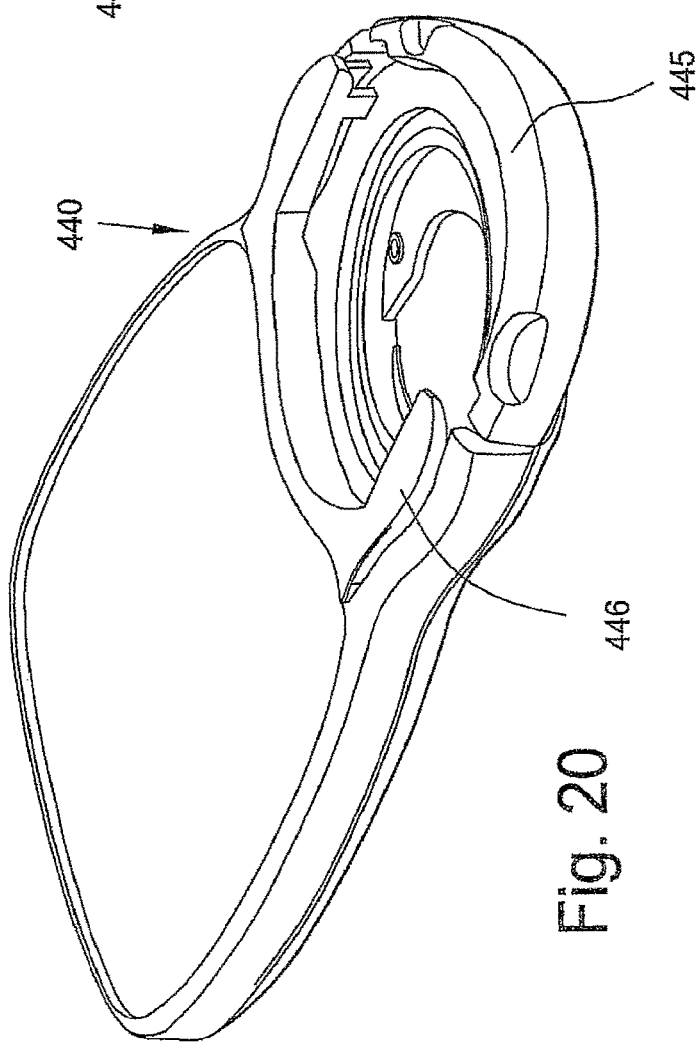

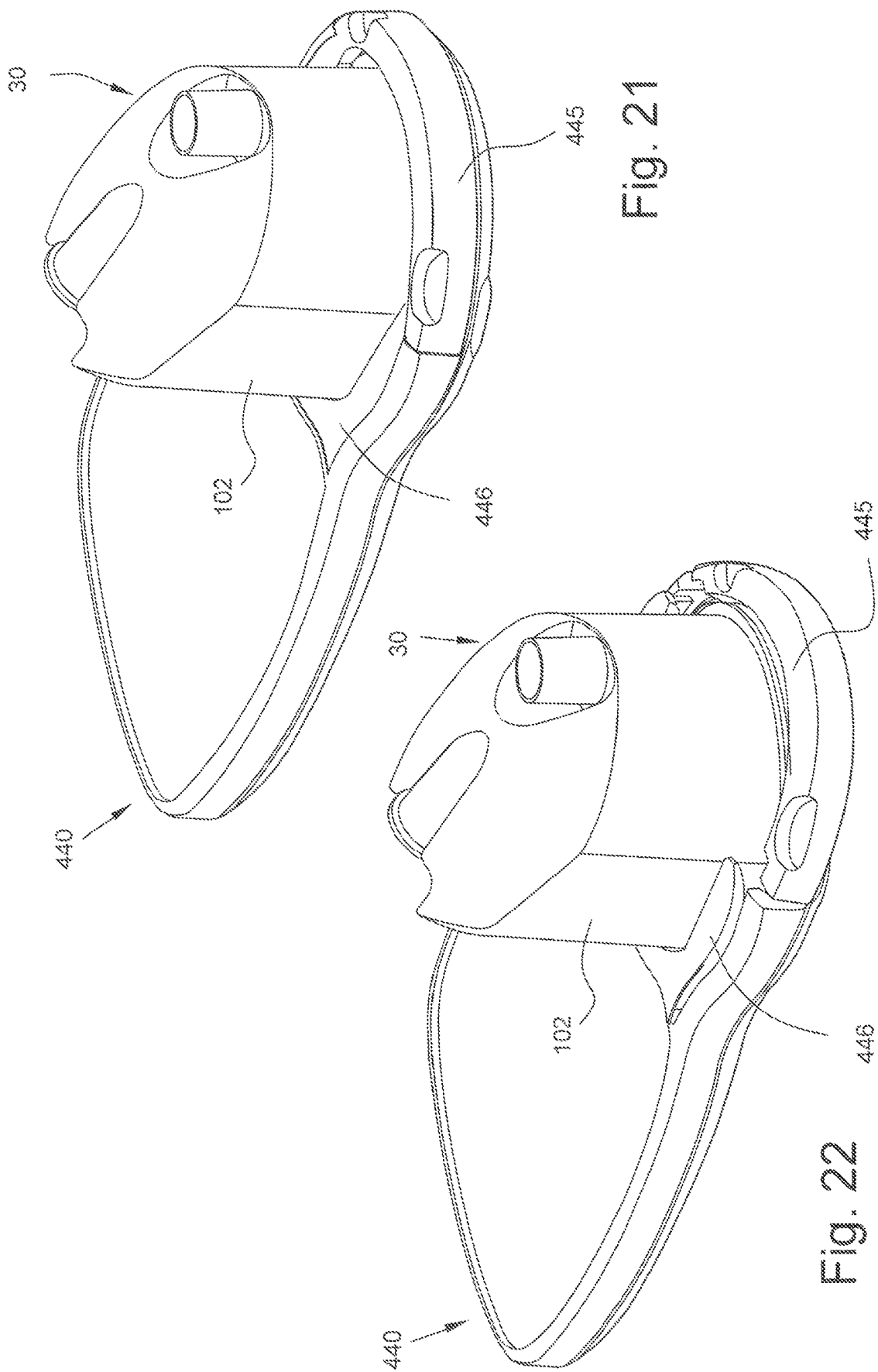

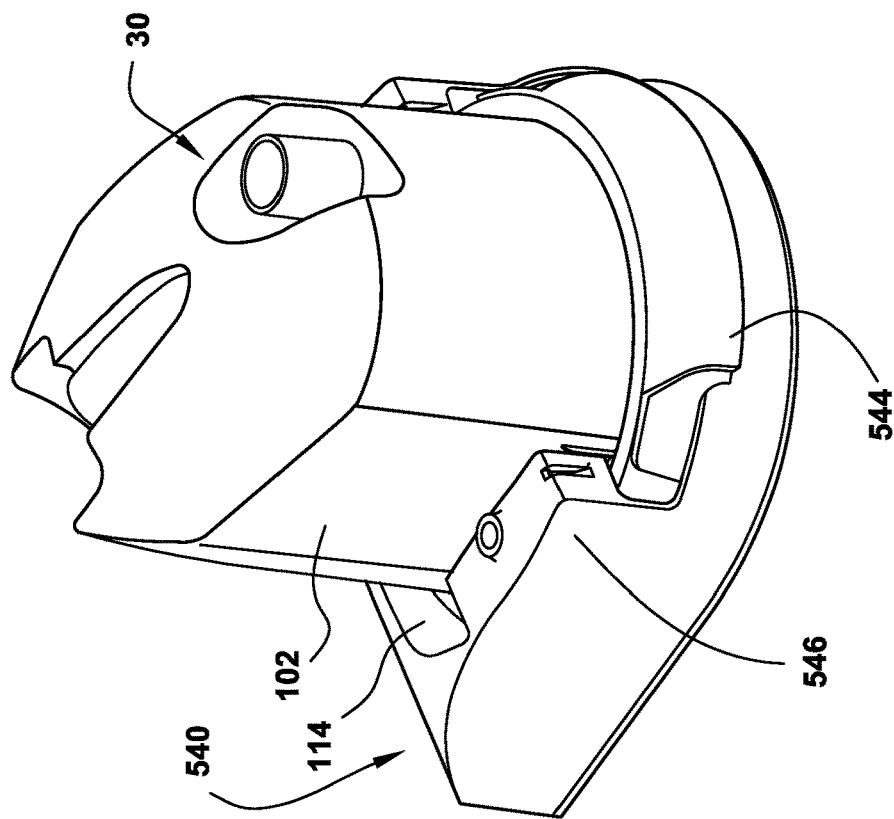
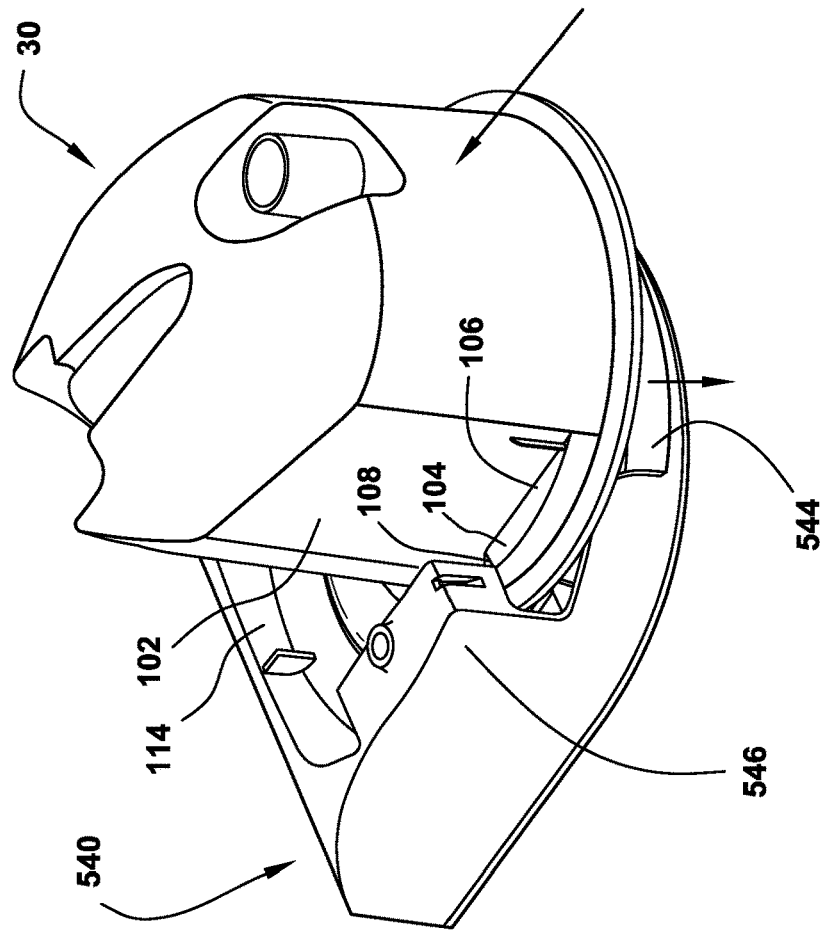

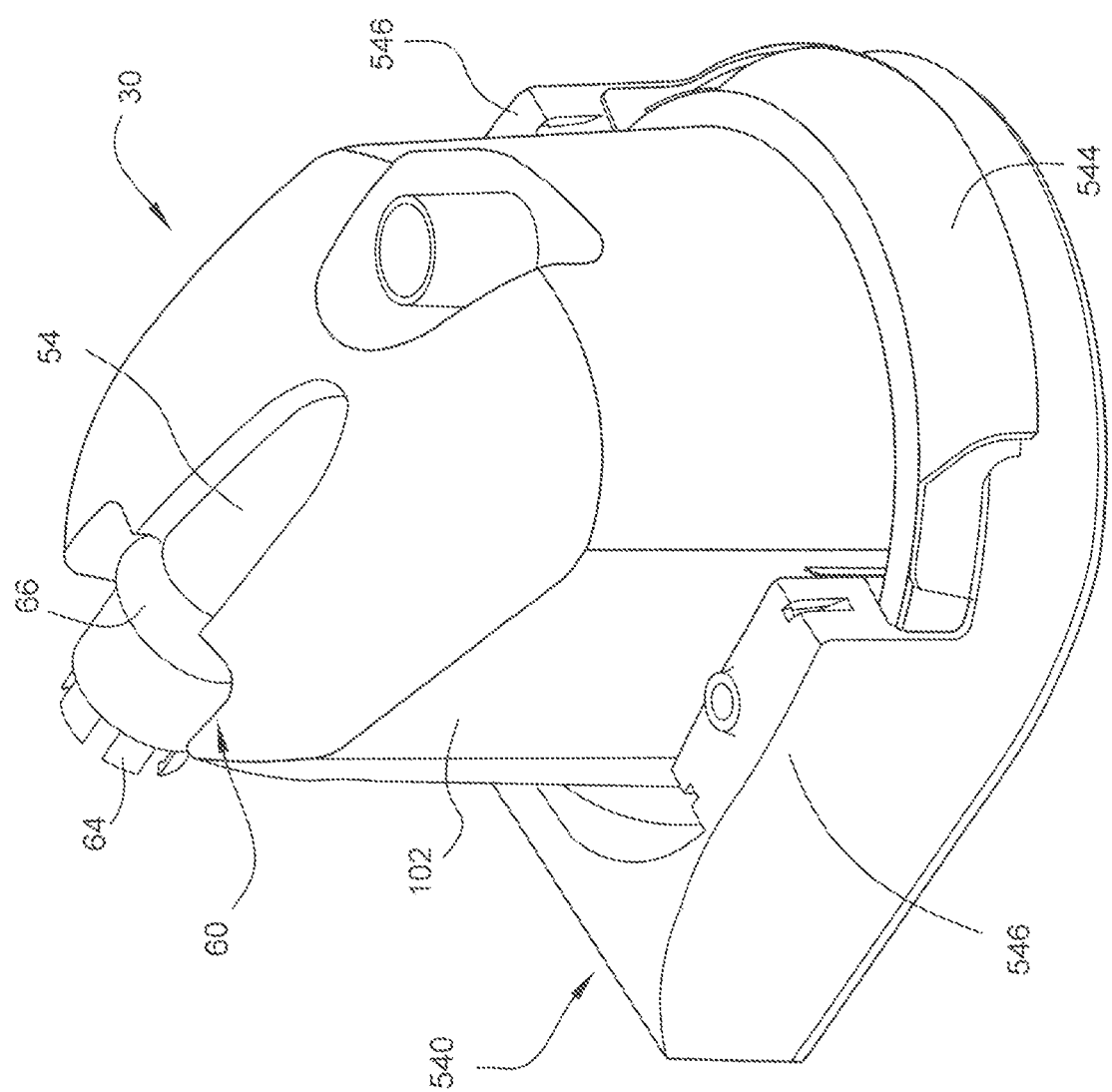

HUMIDIFIER AND/OR FLOW GENERATOR FOR CPAP DEVICE

CROSS-REFERENCE TO PRIORITY APPLICATION

This application is a continuation of U.S. application Ser. No. 14/687,223, now allowed, filed Apr. 15, 2015, which is a continuation of U.S. application Ser. No. 11/988,870, now U.S. Pat. No. 9,038,629, filed Jan. 16, 2008, which is the U.S. national phase of International Application No. PCT/AU2006/001170, which designated the U.S. and claims the benefit to U.S. Provisional Application No. 60/707,948, filed Aug. 15, 2005, the entire contents of each of which are hereby incorporated by reference.

FIELD OF THE INVENTION

The present invention relates to a removable humidifier and/or flow generator for a Continuous Positive Airway Pressure (CPAP) device used to treat sleep disordered breathing (SDB) conditions such as Obstructive Sleep Apnea (OSA).

BACKGROUND OF THE INVENTION

Domestic treatment of OSA and other SDB is usually done using a device that provides CPAP, e.g., nasal CPAP. A common configuration of a treatment system comprises a CPAP device and a patient interface, e.g., a nasal mask. The nasal mask forms a sealing interface with the patient's nasal passages in use so that the supply of air at positive pressure from the CPAP device may be delivered to the patient's airways. In this way, while the patient is wearing a nasal mask, their mouth is uncovered.

In some situations, patients "mouth breath" during sleep. When this happens while wearing only a nasal mask, air can pass in the mask and straight out the patient's mouth. This can lead to drying of the patient's airway and patient discomfort. This patient discomfort can to some extent be alleviated by the use of a humidifier placed between the CPAP device and the patient interface.

Many humidifiers are available, although the most convenient form is one that is either integrated with or configured to be coupled to the relevant CPAP device. While passive humidifiers can provide some relief, generally a heated humidifier is required to provide sufficient moisture to the air so that patients will be comfortable. Humidifiers typically comprise a water tub having a capacity of several hundred milliliters, a heating element, a control to enable the level of humidification to be varied, an air inlet to receive air from the blower, and an air outlet adapted to be connected to an air delivery conduit so that the humidified pressurized air may be passed to the patient interface. Usually, the water tub is removable from the system so that it can be refilled when necessary.

In making a humidification tub removable, there are two problems that need to be overcome. Firstly, there is a need for an air seal between the air outlet of the flow generator and the air inlet of the humidifier tub. An air seal is important to reduce air leaks that may result in an increased pressure drop between the air pressure generated by the flow generator and the air pressure delivered to the patient at the patient interface. Secondly, for efficient humidification, there must be adequate thermal contact between the humidification tub and the heating element.

Commonly, humidifier tubs are attached either directly to a humidifier control base or to a system base or cradle that facilitates the correct assembly of the flow generator with the humidifier. Generally, the humidifier control base or the system base or cradle comprises a heating plate that contacts the base of the humidifier tub to facilitate heating of the water within the humidifier tub. Commonly, these base systems comprise a spring loaded heater plate on to which the humidifier tub is attached. The spring loaded heater plate ensures good thermal contact with the base of the humidifier tub. For example, the Fisher & Paykel HC200 system and the Respironics RemStar heated humidifier have spring loaded heater plates. However, such spring loaded heater plates can provide a friction force against insertion of the humidifier tub, which may make installation of the humidifier tub difficult for some users, especially older or frail users.

SUMMARY OF THE INVENTION

One aspect of the invention relates to a seal between the humidifier inlet and flow generator outlet.

Another aspect of the invention relates to a method and apparatus for retaining a humidifier tub for use in a CPAP device, e.g., nasal CPAP device.

Another aspect of the invention relates to a method and apparatus for providing good thermal contact between the humidifier tub and a heating element.

Another aspect of the invention relates to management of the inadvertent introduction of water into the flow generator, e.g., by tipping or overfilling the humidifier.

Yet another aspect of the invention relates to a CPAP device or humidifier including a humidifier tub including a heat conducting base plate and a cradle to support the humidifier tub in an operative position. The cradle includes a heater plate in communication with the heat conducting base plate of the humidifier tub in use. The cradle further includes a retaining mechanism to retain the humidifier tub in the cradle. The retaining mechanism is structured to force the base plate into engagement with the heater plate.

Another aspect of the present invention relates to a CPAP device including a cradle having a fixed heating plate; and a humidifier tub having a heat conducting base, the base being forcibly coupled with the fixed heating plate of the cradle upon assembly of the cradle and the humidifier tub.

Still another aspect of the invention relates to a method for retaining a humidifier tub to a cradle, comprising providing a cradle including a retaining mechanism; moving the retaining mechanism to a first position that enables insertion of the humidifier tub; providing the humidifier tub to the cradle; moving the retaining mechanism to a second position that secures the humidifier tub in an operative position; and forcing a heat conducting base plate of the humidifier tub into engagement with a heater plate of the cradle.

Another aspect of the invention relates to a CPAP device comprising a flow generator including a flow generator outlet, a motor having a motor outlet, a muffler chamber having an inlet coupled to the motor outlet and a muffler chamber outlet in communication with a flow generator outlet, wherein an axis of the motor outlet is offset from an axis of the muffler chamber outlet and/or the flow generator outlet.

Still another aspect of the invention relates to a CPAP device comprising a flow generator including a flow generator outlet, a motor having a motor outlet, a muffler chamber having an inlet coupled to the motor outlet and a muffler chamber outlet in communication with a flow generator outlet, wherein said muffler chamber includes an upper part conduit portion and a lower storage portion integrally formed with the part conduit portion.

These and other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIG. 7 is a cross section along section 7-7 of FIG. 5;

FIGS. 9-12 illustrate a cradle according to an embodiment of the present invention using a catch to secure the humidifier tub;

FIG. 13 illustrates a cradle according to another embodiment of the present invention using a sliding docking portion to secure the humidifier tub;

FIGS. 14A, 14B, and 15 illustrate a cradle according to another embodiment of the present invention using a pivoting docking portion to secure the humidifier tub;

FIGS. 17-22 illustrate a cradle according to another embodiment of the present invention using a pivotable front guard and a pivotable humidifier retaining portion;

FIGS. 23-25 illustrate a cradle according to another embodiment of the present invention using a front guard and at least two pressure pads;

FIG. 26 illustrates a humidifier tub secured to the cradle shown in FIGS. 23-25, the humidifier tub engaged with the seal/connector shown in FIGS. 5-7;

DETAILED DESCRIPTION OF ILLUSTRATED EMBODIMENTS

1. CPAP Device

FIGS. 1-4 illustrate a CPAP device 10 according to an embodiment of the present invention. As illustrated, the CPAP device 10 includes a flow generator 20 and a humidifier 30 adapted to be coupled to the flow generator 20.

The humidifier may be connected to the flow generator using loop-back power and communication cables between the humidifier and the flow generator. In an alternative, the humidifier and the flow generator may communicate using a fiber optic or infrared communication system between the flow generator and the humidifier. This system may detect the presence of the humidifier tub and provide communication and power between the devices via transmitters and receivers.

2. Humidifier

Figure 9:
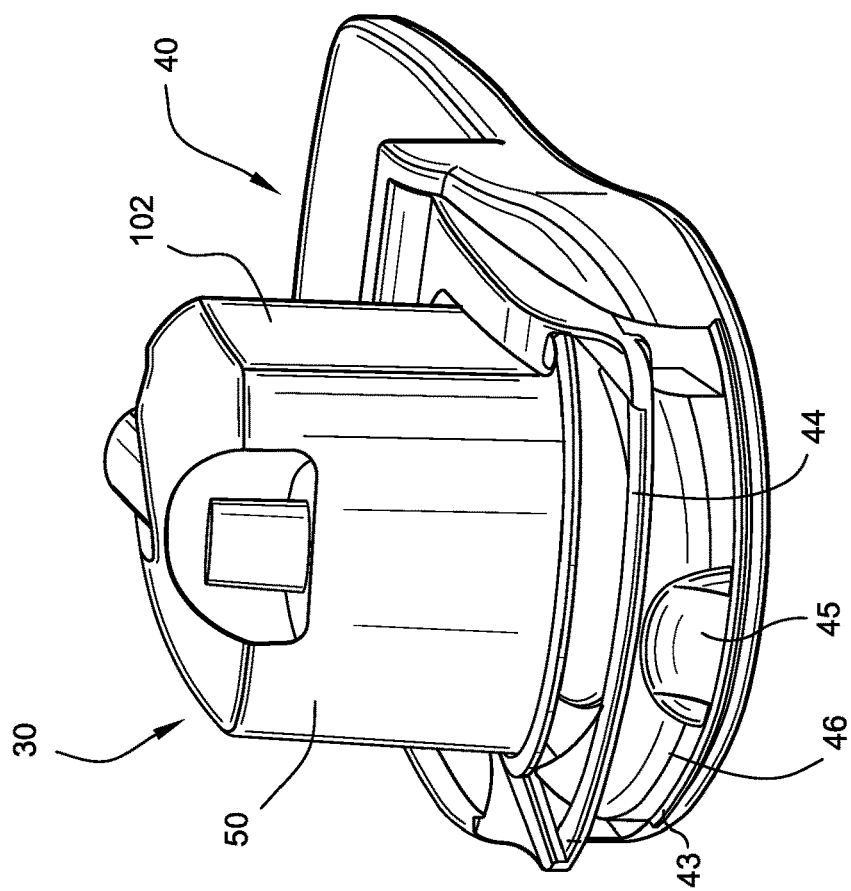

The humidifier 30 includes a tub or (humidifier tub) 50 having a base plate 52 sealed to the bottom of the tub 50 and a heater element that may be formed as part of a cradle (or cradle unit) unit 40 (see FIG. 9). The heater element may also be formed as an integral part of the base plate or otherwise separate from the cradle. The tub 50 includes an inlet 54 adapted to be in fluid communication with (i.e. not necessarily directly) the outlet 24 of the flow generator 20, and an outlet 56 adapted to be connected to an air delivery conduit. The air delivery conduit includes one end coupled to the outlet 56 of the tub 50 and an opposite end coupled to a patient interface. The patient interface comfortably engages the patient's face and provides a seal. The patient interface may have any suitable configuration as is known in the art, e.g., full-face mask, nasal mask, oro-nasal mask, mouth mask, nasal prongs, etc.

The tub 50 and base plate 52 define a chamber that is adapted to receive a volume of water, e.g., several hundred milliliters. The inlet 54 and the outlet 56 are both in communication with the chamber. In use, a supply of pressurized air from the flow generator 20 enters the inlet 54 of the tub 50 and collects moisture through contact with the water within the tub 50 before continuing on to the outlet 56 and to the patient via the air delivery conduit.

Figure 1:
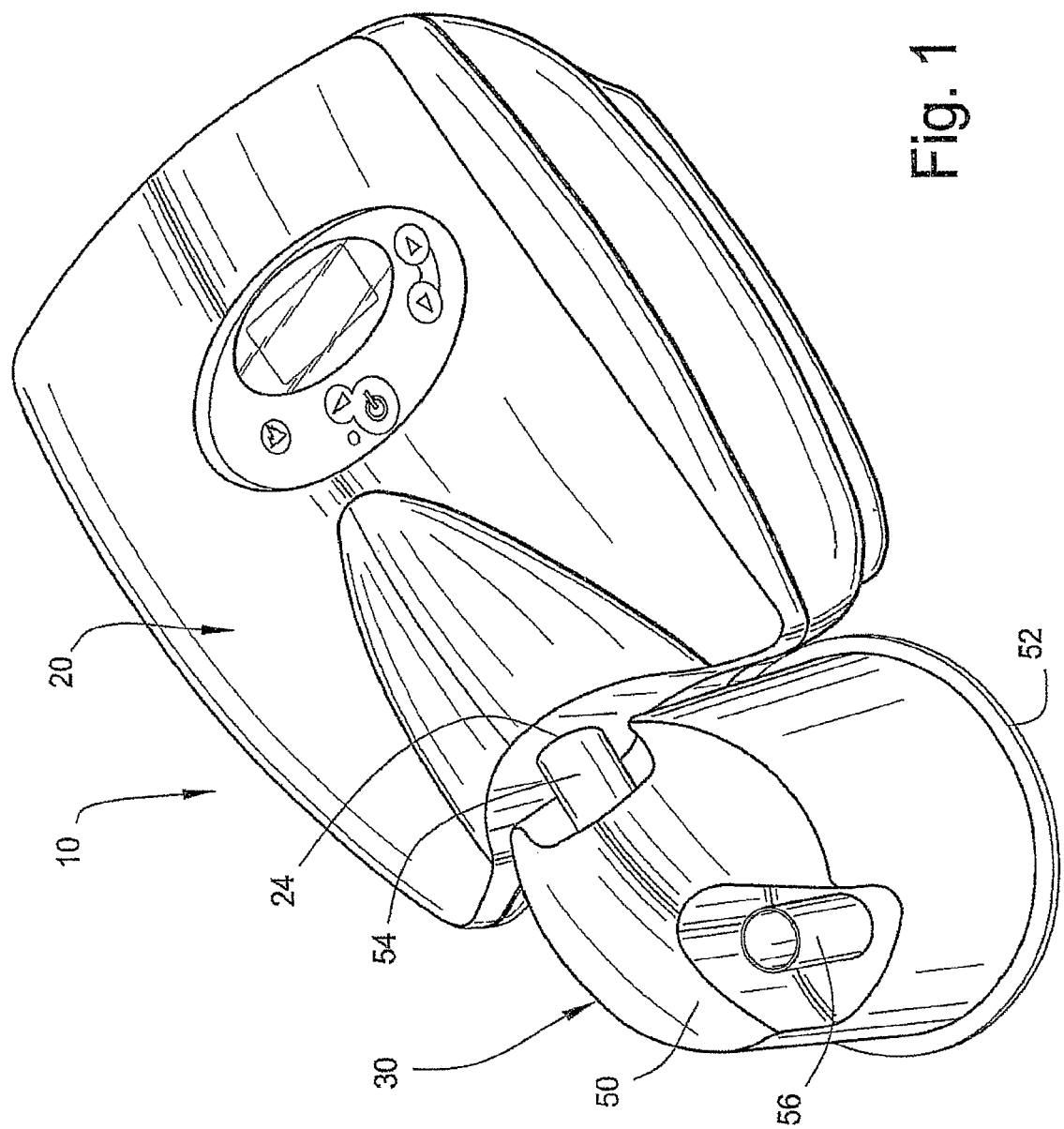
FIG. 1 is a perspective view of a CPAP device according to an embodiment of the invention.
Figure 2:
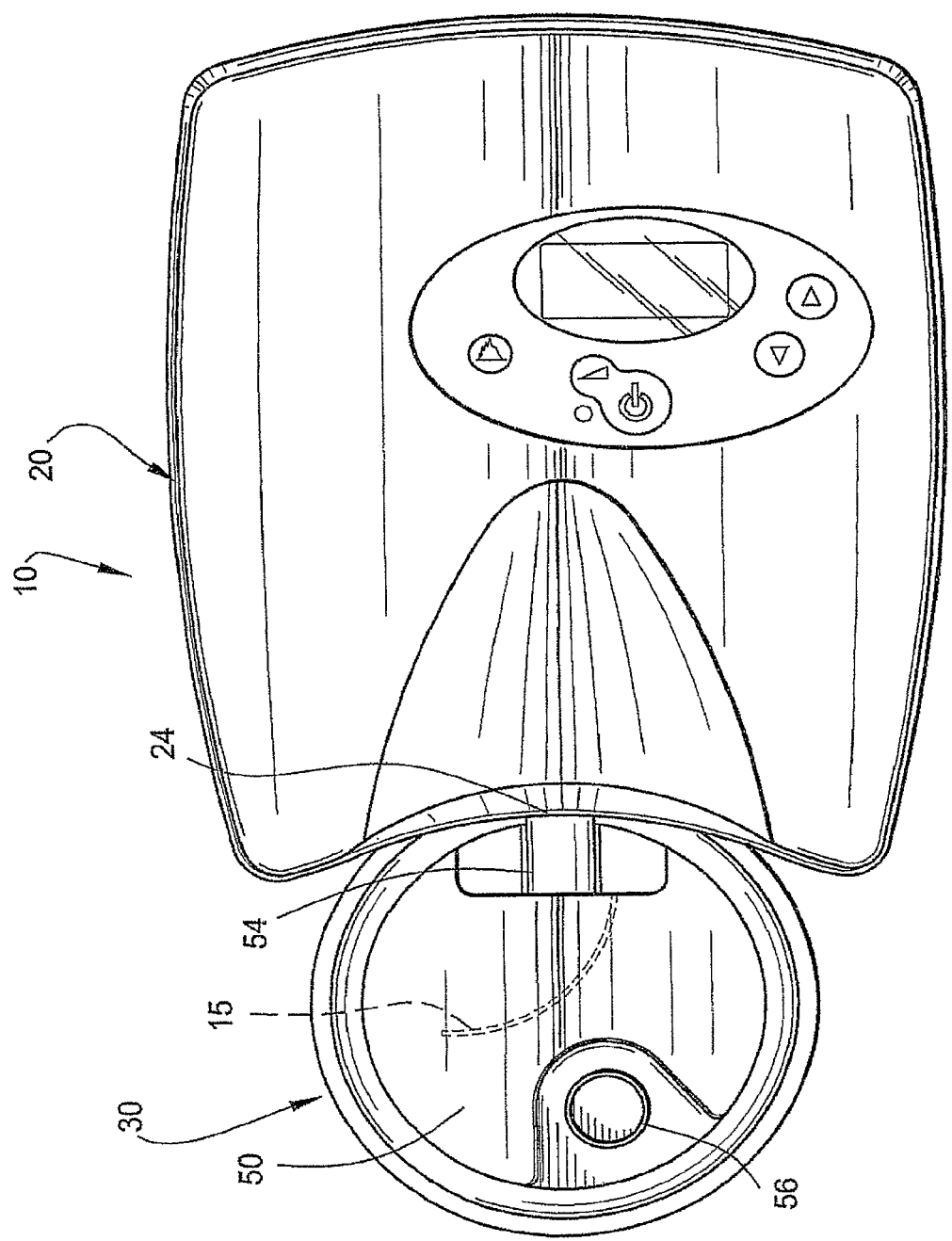
FIG. 2 is a top view of the CPAP device shown in FIG. 1.
Figure 3:
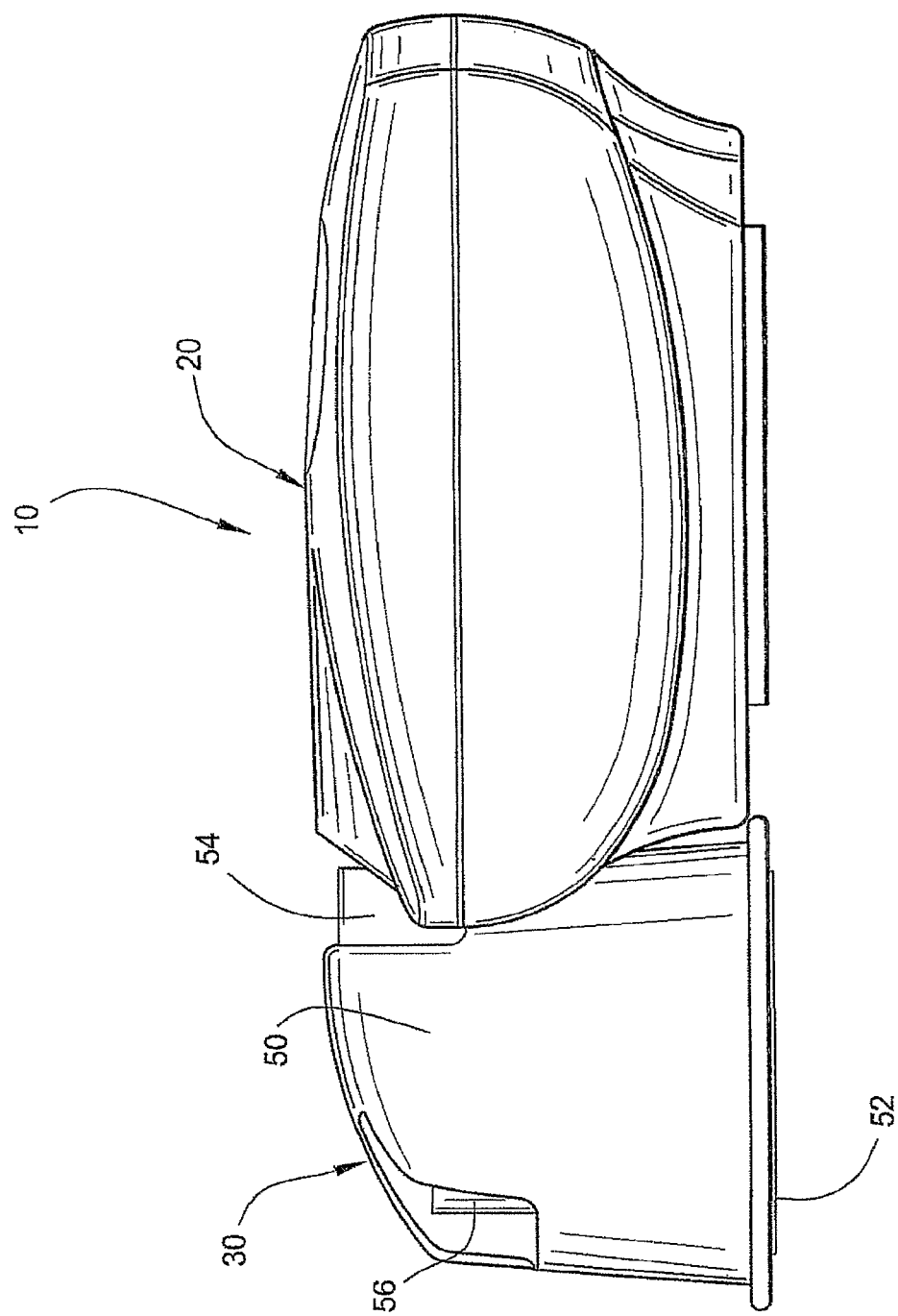
FIG. 3 is a side view of the CPAP device shown in FIG. 1.
Figure 4:
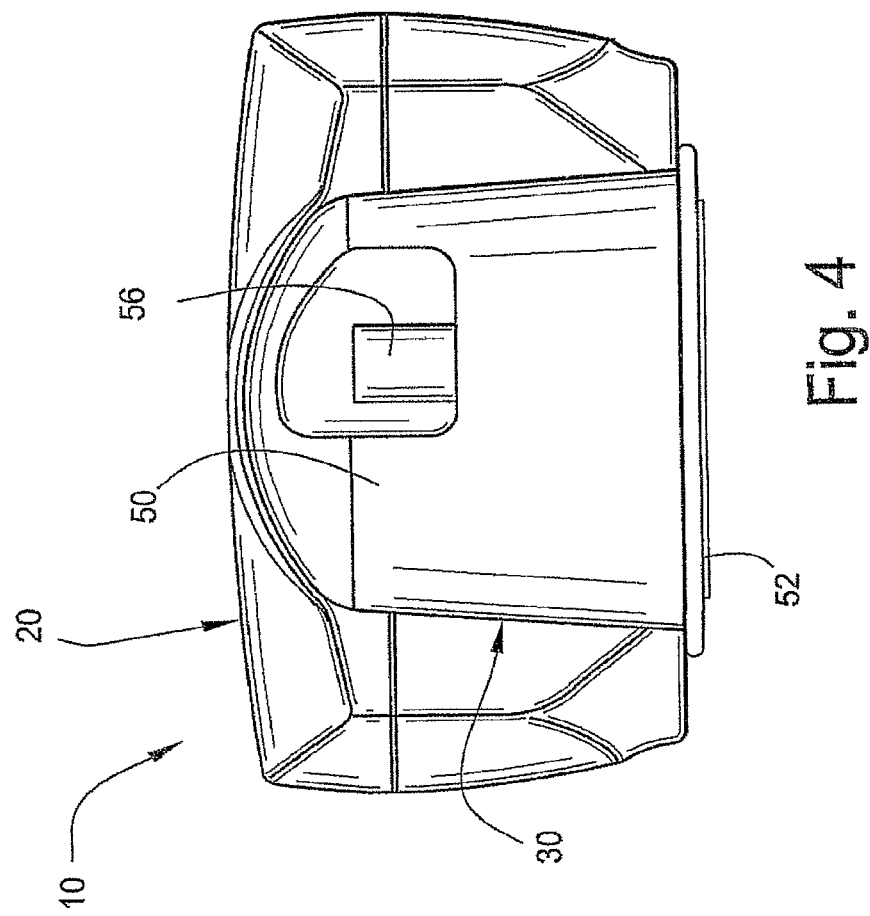
FIG. 4 is an end view of the CPAP device shown in FIG. 1.

As best shown in FIG. 2, the tub 50 may include a curved baffle 15 adjacent the outlet end of the inlet 54 to smoothly change the direction of the air flow by gently guiding the air flow around the tub 50 while limiting the loss of pressure. Also, the base plate 52 may be in the form of a heat conducting base plate. Specifically, the base plate 52 may be formed of a heat conducting material, e.g., aluminum sheet.

Figure 23:
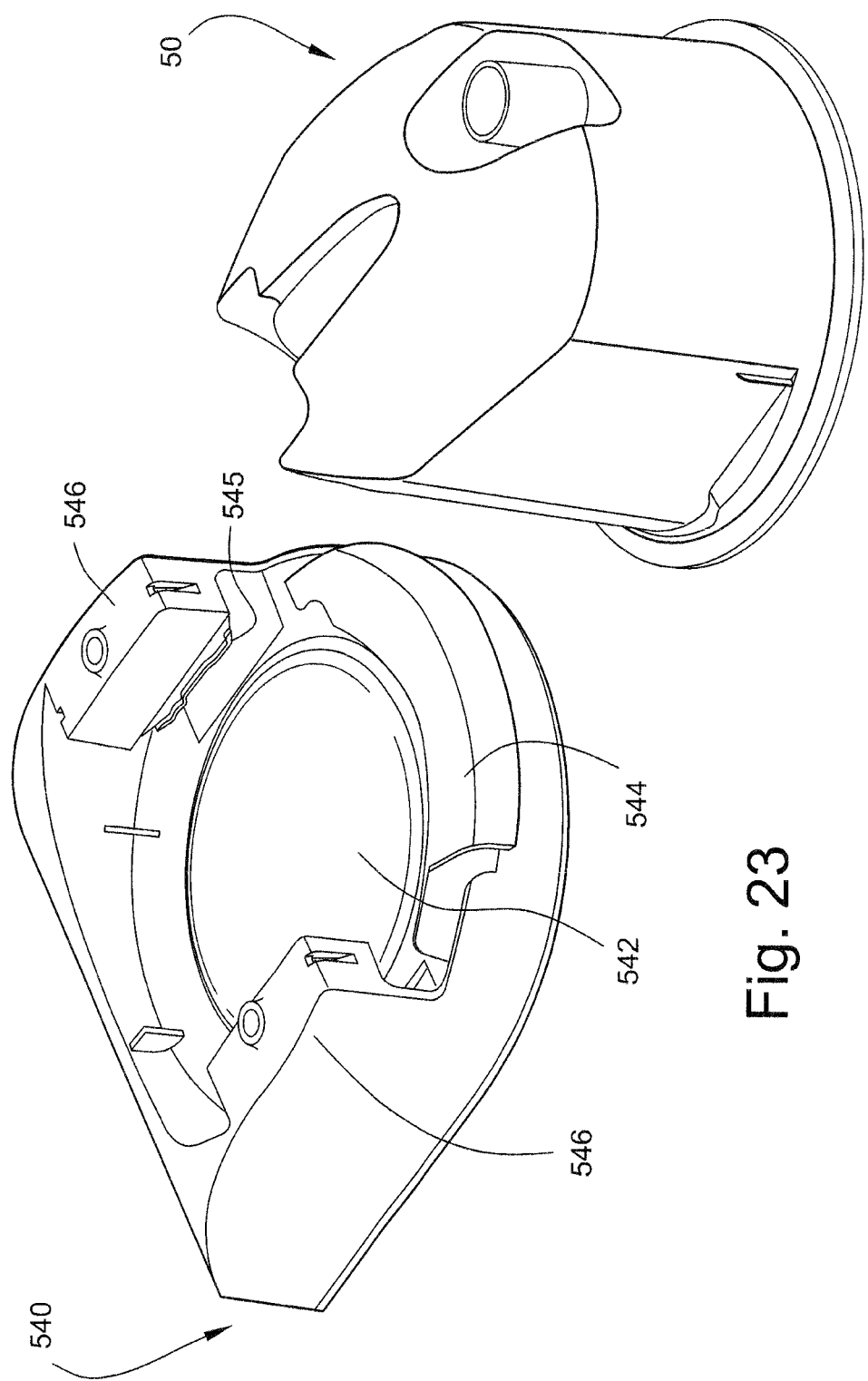

In addition, as best shown in FIG. 23, the tub 50 may include upstanding generally planar side walls 102 and a rear wall 112. The tub 50 may also include a shoulder 104 extending horizontally outwards from a lower portion of each upstanding generally planar side wall 102 of the humidifier tub. Each shoulder 104 may include a main portion 106 and a ramped portion 108. The main portion 106 may have a substantially level upper surface, while an upper surface of the ramped portion 108 may taper down toward the rear wall 112 of the humidifier tub 50.

In an embodiment, the humidifier 30 and tub 50 may be structured such as the humidifier and tub described in U.S. Patent Application No. 60/707,949, entitled "Humidifier Tub For CPAP Device", filed Aug. 15, 2005, the contents of which are incorporated in its entirety by reference herein. Also, in an embodiment, the flow generator 20 may be structured and controlled such as the flow generator described in U.S. Patent Application No. 60/707,951, entitled "Low Cost CPAP Flow Generator and Humidifier Assembly", filed Aug. 15, 2005, the contents of which are incorporated in its entirety by reference herein.

3. Seal Between Humidifier and Flow Generator

Figure 5:
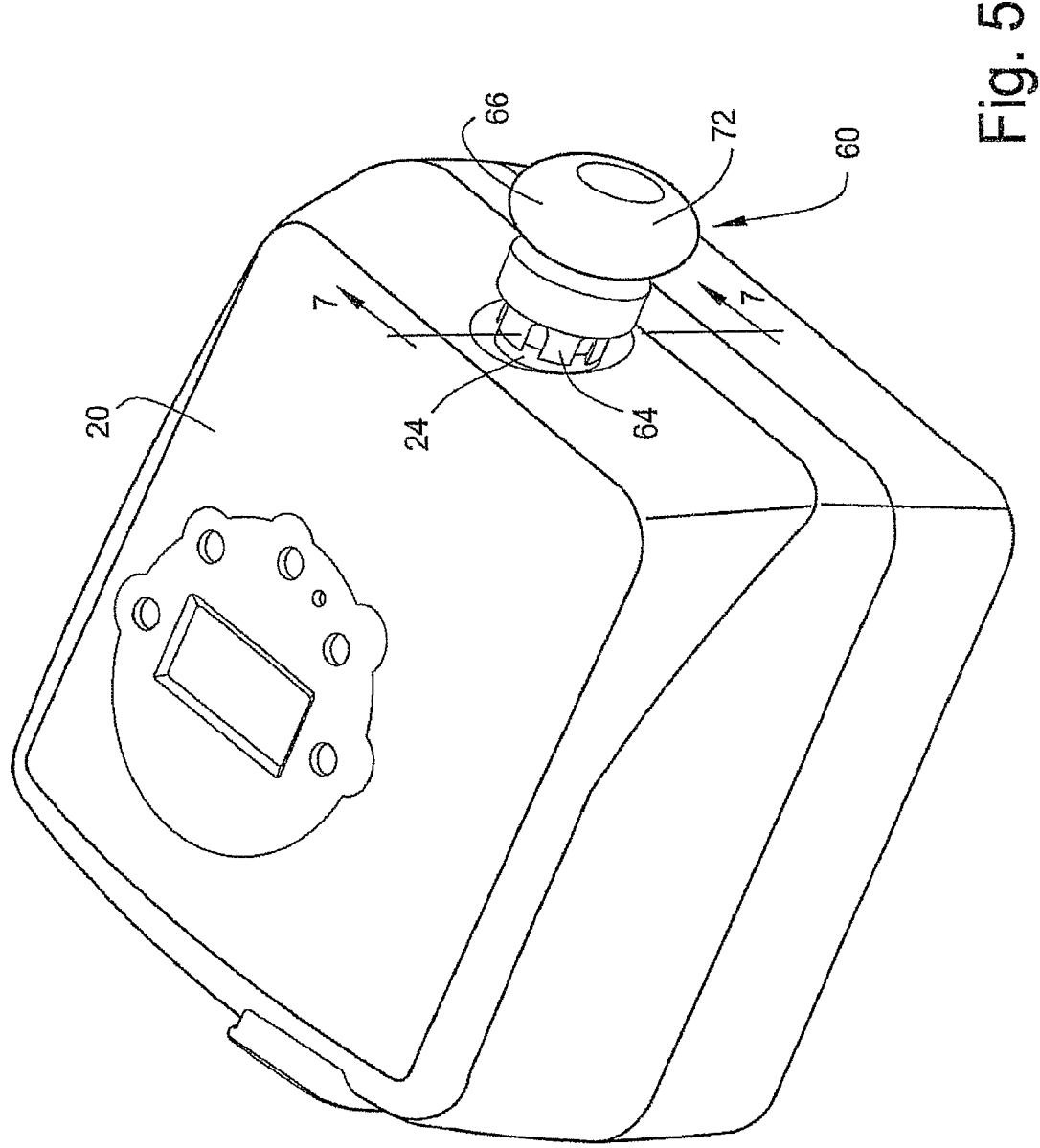
FIG. 5 illustrates a blower with a seal/connector according to an embodiment of the present invention.
Figure 6:
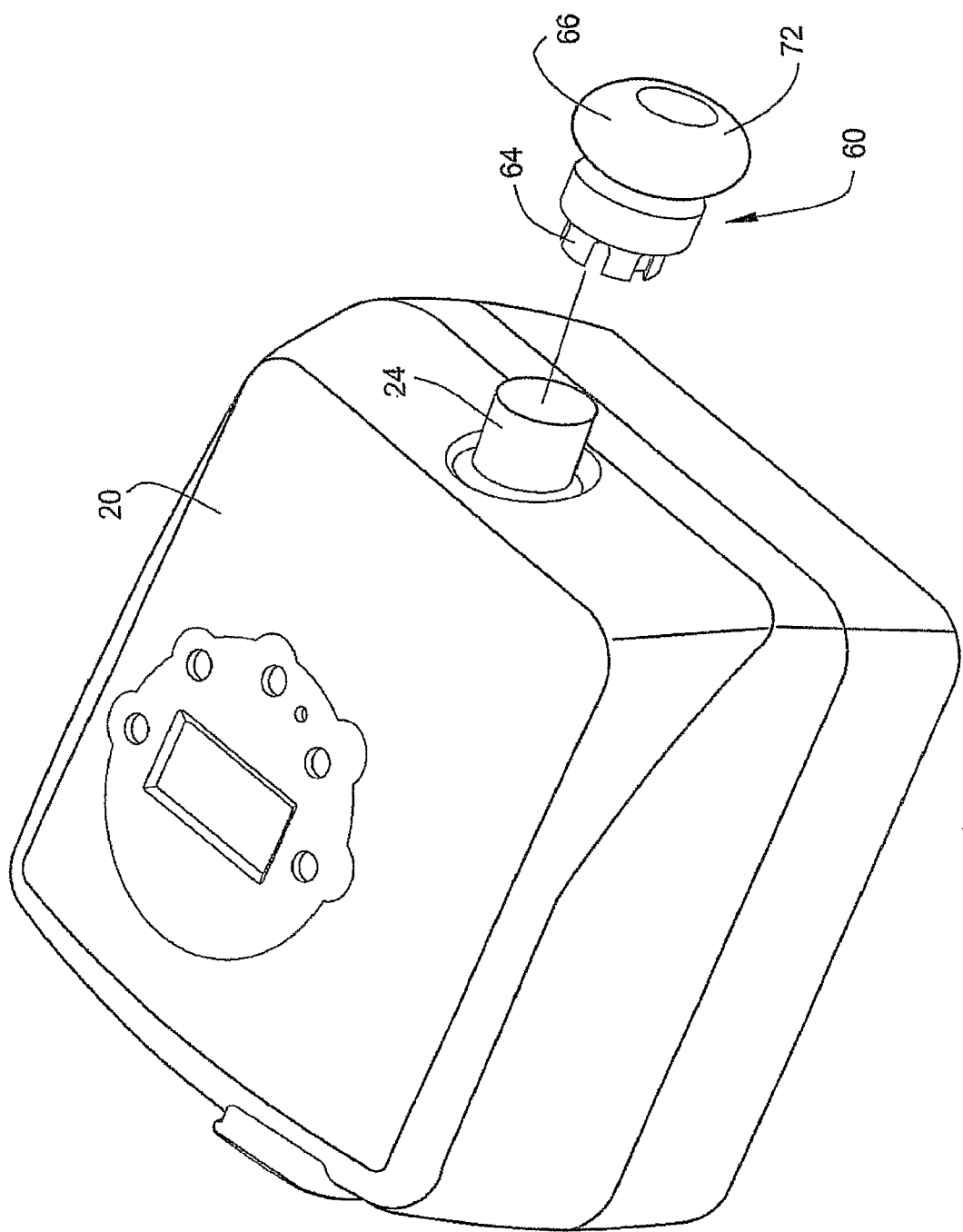
FIG. 6 illustrates the blower and seal/connector of FIG. 5 in an exploded position.

FIGS. 5-7 illustrates a connector 60 according to an embodiment of the present invention. The connector 60 interconnects the outlet 24 of the flow generator 20 and the inlet 54 of the tub 50. Moreover, the connector 60 provides a pressure-activated or 'self-energizing' face seal that provides a seal between the flow generator 20 and the tub 50. The seal accommodates misalignment and manufacturing tolerances as described below.

As illustrated, the connector 60 provides a channel 62 (FIG. 7) to deliver pressurized air from the flow generator 20 to the humidifier tub 50. In the illustrated embodiment, the connector 60 is removably attached to the flow generator 20 and is structured to sealingly engage with the inlet 54 of the tub 50.

As best shown in FIG. 7, the connector 60 includes two components that are coupled to one another. Specifically, the connector 60 includes a firm frame attaching portion 64 and a flexible sealing portion 66. The firm frame attaching portion 64 is preferably constructed of a plastic material and includes an attachment structure that enables secure attachment to the outlet 24 of the flow generator 20. For example, the attachment structure may be in the form of a snap-fit clip that includes one or more protrusions 68 adapted to engage within a corresponding groove 70 provided in the outlet 24 with a snap fit, as shown in FIG. 7. However, the attachment structure may have other suitable configurations.

The flexible sealing portion 66 comprises a face seal (or bellows-type conforming face seal) 72 preferably made from silicone or other similar material that does not provide problems with creep in use. The bellows-type conforming face seal 72 comprises an aperture 74 that is adapted to abut the inlet 54 of the humidifier tub 50. The flexible sealing portion 66 further includes an internal sealing element 76, e.g., wiper seal, that independently seals to the outlet 24 of the flow generator 20 to prevent air leakage through the connection between the flow generator 20 and the humidifier 30. Any means of providing a seal between the flow generator 20 and humidifier 30 is encompassed within the scope of the invention. For example, the internal sealing element 76 may be in the form of a compression sealing ridge or a wiper seal. The flexible sealing portion 66 is constructed such that it preferably does not have any split lines (from the tooling) on the outer sealing face that may interfere with obtaining a satisfactory pressure seal.

In addition, the flexible sealing portion 66 includes an interlocking structure that is structured to interlockingly engage a complementary interlocking structure provided on the firm frame attaching portion 64. In the illustrated embodiment, the sealing portion 66 includes a groove 78 that interlocks with a protrusion 80 provided on the frame attaching portion 64. This arrangement interlocks the sealing portion 66 to the frame attaching portion 64. However, the sealing portion 66 may be coupled to the frame attaching portion 64 in other suitable manners.

Figure 8A:
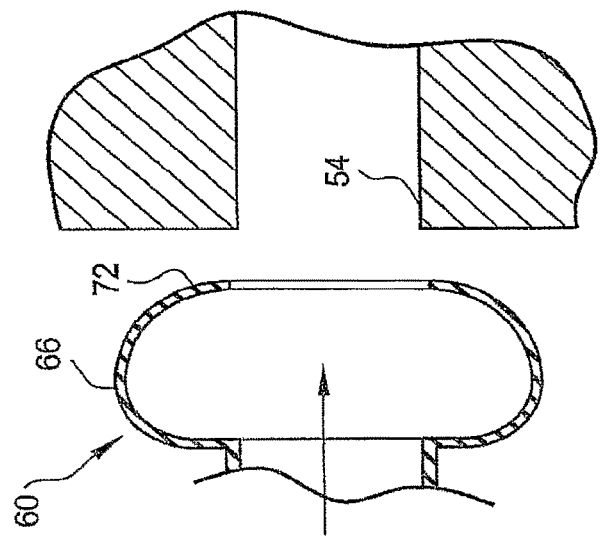
FIG. 8A is a cross-sectional view illustrating a seal/connector according to another embodiment of the present invention.

Alternatively, the entire connector 60 may be made of silicone or a silicone-like material with differing rigidity characteristics for the firm frame attaching portion 64 and the flexible sealing portion 66. For example, as shown in FIG. 8A, the connector 60 may have a one-piece construction and the frame attaching portion 64 may have a cylindrical structure adapted to sealingly engage the outlet 24 of the flow generator 20.

Preferably, the connector 60 has a round shape to provide minimal out-of-mold distortion. The face seal 72 of the flexible sealing portion 66 has approximately 2 mm to 3 mm interference from the nominal contact point to ensure sufficient contact when the connector 60 is pushed against the inlet 54 of the humidifier tub 50. The aperture 74 in the face seal 72 may be larger than the inlet 54 of the tub 50 in order to accommodate the various misalignment and manufacturing tolerances of the connector 60 to outlet 24 of the flow generator 20, to ensure sufficient passage of air flow through the connector 60.

Advantageously, the face seal 72 provides for tolerance in movement in all directions while aligning the humidifier tub 50 and the flow generator 20. For example, the face seal 72 is flexible axially (forwards and backwards), laterally (upwards, downwards, and/or sideways), angularly, pivotally, and/or rotationally. Preferably, the face seal is flexible in all directions, although it may be more flexible in some but more rigid in others.

The face seal 72 may be flexible within a predetermined range. For example, the face seal 72 may be axially and/or laterally flexible within a range of about 1-5 mm, preferably about 2-3 mm. However, the face seal 72 may be axially and/or laterally flexible less than 1 mm or greater than 5 mm. Also, the face seal 72 may be angularly, pivotally, and/or rotationally flexible within a range of about 1-10°, preferably about 3-6° or about 5°. However, the face seal 72 may be angularly, pivotally, and/or rotationally flexible less than 1° or greater than 10°.

In use, the firm frame attaching portion 64 of the connector 60 is securely attached to the outlet 24 of the flow generator 20 and the bellows-type conforming face seal 72 on the flexible sealing portion 66 protrudes therefrom. The air inlet 54 of the humidifier tub 50 is positioned adjacent to or abutting the face seal 72. When pressurized air flows out through the outlet 24 of the flow generator 20, the face seal 72 fills with air and establishes a pressurized face seal with the inlet 54 of the humidifier tub 50.

Figure 8B:
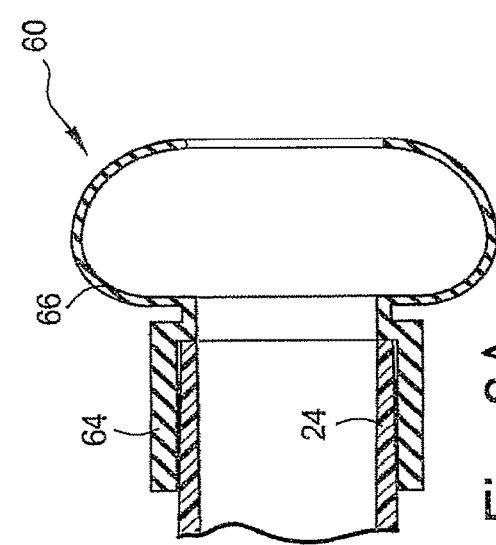
FIGS. 8B-8C illustrate a seal/connector according to an embodiment of the present invention in use.
Figure 8C:
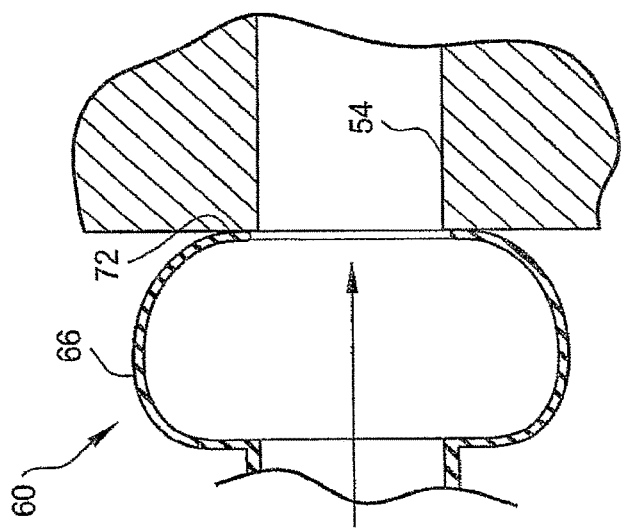
Figure 10:
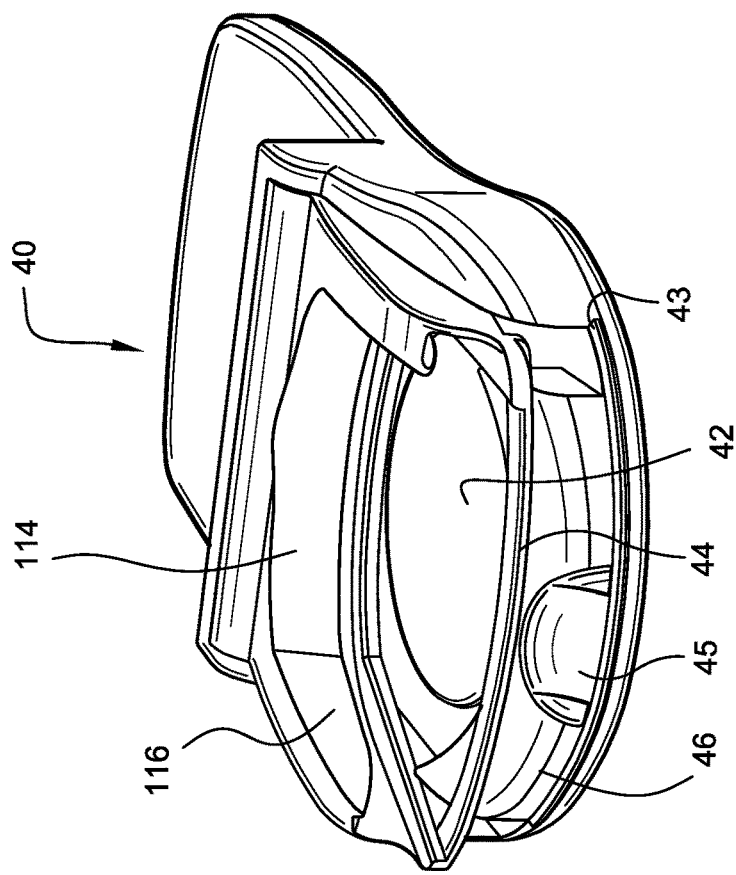

FIGS. 8B and 8C illustrate an embodiment of the connector 60 forming a seal with the inlet 54 of a humidifier tub. As shown in FIG. 8B, the connector 60 is positioned adjacent the inlet 54 such that the bellows-type conforming face seal 72 is spaced from the inlet 54. As pressurized air flows out through the outlet of the flow generator (as indicated by the arrow), the face seal 72 fills with air and expands into engagement with the axial end or axially facing surface of the inlet 54 as shown in FIG. 8C. That is, the face seal 72 balloons outwardly to form a cylindrical face seal with the inlet 54.

The bellows-type conforming face seal 72 provides a flexible bellows or gusset that allows the face seal 72 to self align with the inlet 54. That is, the flexibility and freedom of movement of the face seal 72 (e.g., in all directions within a predetermined range) allows the face seal 72 to form a seal with the inlet 54 even if they are misaligned. Specifically, the face seal 72 can still form a seal with the inlet 54 even if the axis of the connector 60 is not aligned with the axis of the inlet 54. This arrangement accommodates the various misalignments that may occur between the connector 60 and the inlet 54.

Although the connector 60 has been described as being attached to the outlet 24 of the flow generator 20, in an alternative embodiment the connector 60 may be attached to the inlet 54 of the humidifier tub 50 and the flexible sealing portion 66 may abut the outlet 24 of the flow generator 20. In a further embodiment, the connector 60 may be permanently attached to either the outlet 24 of the flow generator 20 or the inlet 54 of the humidifier tub 50. However, the connector 60 is preferably a separate component that can be easily replaced or removed for cleaning or sterilization purposes.

4.0 Mechanism for Retaining Humidifier in Cradle

The CPAP device 10 may include a cradle (e.g., cradle 40 in FIGS. 9-12) structured to support the humidifier tub 50 in an operative position with respect to the flow generator 20. The cradle may include a front wall 114, side walls 116 and a heater plate that includes a heating element, e.g., a ceramic heating element. In use, the cradle receives the humidifier tub 50 so that the heating element is in thermal contact with the heat conducting base plate 52 (FIG. 3) of the humidifier tub 50. This arrangement allows water contained within the humidifier tub 50 to be heated to provide sufficient moisture to the air so that patients will be comfortable. In addition, the front wall 114 of the cradle faces the rear wall 112 of the humidifier tub 50 when the humidifier tub 50 is docked within the cradle 40. Also, the side walls 116 of the cradle 40 are configured to face the generally planar side walls 102 of the humidifier tub 50 such that the humidifier tub 50 is properly aligned with respect to the cradle 40 as the humidifier tub 50 is slid in the assembly direction (FIGS. 9-12 and 23-26).

The cradle may provide one or more of the following functional features for the humidifier tub 50: allow the humidifier tub 50 to be correctly oriented with respect to the flow generator 20; securely lock the humidifier tub 50 within the cradle such that it cannot be easily pulled out during use; ensure good thermal contact between the humidifier tub 50 and the heater plate present in the cradle; allow easy docking of the humidifier tub 50, especially for frail, elderly users; and for safety reasons, limit access to hot areas of the humidifier chamber when heat is being transferred from the heater plate to the heat conducting base plate 52 of the humidifier tub 50, once the humidifier tub 50 is docked within the cradle.

Advantageously, the cradle as described in the various embodiments herein pushes the humidifier tub downwards onto a fixed heater plate rather than forcing the heater plate upwards against the humidifier tub. The fixing of the hot plate in the cradle improves and simplifies the electrical ensures that the hot plate is sealed against water entry, which sealing is more difficult if the hot plate is movably mounted on the cradle. In this type of arrangement, a spring that forces the humidifier tub into engagement with the heater plate may be disengaged during installation of the humidifier tub within the cradle. The disengagement of the spring reduces friction forces for installation thus making installation easier and consequently minimizing friction damage to the heater plate, cradle, and humidifier tub. After installation of the humidifier tub, the spring may be reengaged to simultaneously secure the humidifier tub within the cradle and force the base plate of the humidifier tub against the heater plate to provide good thermal contact between them.

4.1 Cradle with Securing Catch

FIGS. 9-12 illustrate a cradle 40 according to an embodiment of the present invention. As illustrated, the cradle 40 has a securing catch 44 that lifts up and down to enable release or insertion of the humidifier tub 50. The securing catch 44 may be hinged. The lifting up of the securing catch 44 also disables or releases a spring that pushes the humidifier tub 50 down against the heater plate 42 (see FIGS. 9 and 10). After insertion of the humidifier tub 50 along the arms of the catch 44, closure of the catch 44 re-engages the spring to ensure a good thermal connection between the humidifier tub 50 and the heater plate (see FIGS. 11 and 12). Releasing the spring (e.g., by lifting the catch) substantially reduces the forces that have previously acted against freely inserting or removing the humidifier tub. The catch 44 also locks the humidifier tub 50 within the cradle 40 such that it cannot be pulled out during use, e.g., by pulling the air delivery tube. Specifically, a stop 46 is positioned in front of the humidifier tub 50 when the catch 44 is closed to lock the humidifier tub in place. Also, the stop 46 may provide a ridge or protrusion 43 adapted to lock the catch 44 in a closed position. In addition, a groove 45 may be provided in the stop 46 to provide a finger access that facilitates access to the catch 44. The catch 44 also prevents access to the hot heater plate 42 when the humidifier tub 50 is inserted, especially access to the front of the hot heat conducting base plate 52. The gaps between the sides of the tub and the cradle are smaller than the size of a finger (or less) to prevent accidental burning of the patient. The catch provides a "clicking" sound when the tub is properly docked thereby providing audio/tactile feedback to the patient.

4.2 Cradle with Sliding Docking Portion

FIG. 13 illustrates a cradle 240 according to another embodiment of the present invention. In this embodiment, the cradle 240 includes a docking portion 244 that is slidable between a humidifier tub locking position and a humidifier tub unlocking position (FIG. 13). The slidable mechanism may be similar to that used in loading a CD or DVD, for example, and may include a spring to facilitate movement into the humidifier tub unlocking position. In the humidifier tub unlocking position as shown in FIG. 13, the docking portion 244 is slidably extended from the cradle 240 to enable release or insertion of the humidifier tub 50. In the humidifier tub locking position, the docking portion 244 is slidably retracted into the cradle 240 to secure the humidifier tub 50 to the cradle 240. In the illustrated embodiment, the docking portion 244 includes a pin 241 that is adapted to releasably engage a ramp 243 provided on the cradle 240 to releasably lock the docking portion in the humidifier tub locking position. However, the docking portion 244 may be locked in other suitable manners. Also, a spring-loaded arm 246 may be provided to ensure a good thermal connection between the humidifier tub 50 and the heater plate of the cradle 240.

4.3 Cradle with Pivoting Docking Portion

Figure 15:
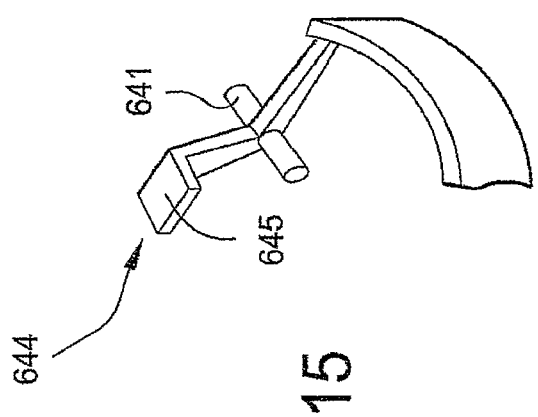

FIGS. 14A, 14B, and 15 illustrate a cradle 640 according to another embodiment of the present invention. In this embodiment, the cradle 640 includes a docking portion 644 that is pivotable about a hinge 641 between a humidifier tub locking position (FIG. 14A) and a humidifier tub unlocking position (FIG. 14B). The cradle 640 includes a spring 648 that biases the docking portion 644 into the humidifier tub locking position. In the humidifier tub unlocking position as shown in FIG. 14B, the docking portion 644 is pivoted downwardly against bias from the spring 648 to enable release or insertion of the humidifier tub 50. In the humidifier tub locking position as shown in FIG. 14A, the docking portion 644 is pivoted upwardly by the spring 648 to secure the humidifier tub 50 to the cradle 640. FIG. 15 is an isolated view of the docking portion 644 and illustrates retaining members 645 that push down on the humidifier tub 50 (e.g., the lateral edges).

4.4 Cradle with Spring-Biased Clamping Edge

Figure 16:
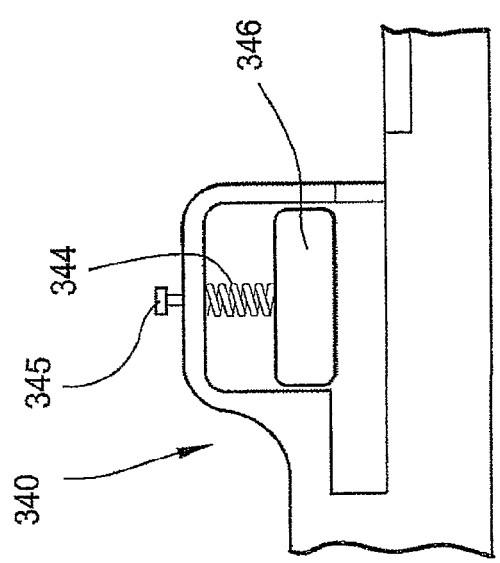
FIG. 16 illustrates a cradle according to another embodiment of the present invention using a spring-biased clamping edge to secure the humidifier tub.

FIG. 16 illustrates a cradle 340 according to another embodiment of the present invention. In this embodiment, a lever or button (e.g., an actuator button 345) is provided on the cradle 340 that is adapted to release a spring 344 connected with a clamping edge 346, e.g., a pressure pad. In use, the humidifier tub 50 is inserted into the cradle 340 and the lever or button is actuated to release the spring-biased clamping edge 346 which clamps or frictionally secures the base of the humidifier tub 50 between the cradle 340 and the clamping edge 346. The clamping edge 346 provides downwardly directed pressure to ensure good thermal contact between the base of the humidifier tub 50 and the heater plate.

Figure 17:
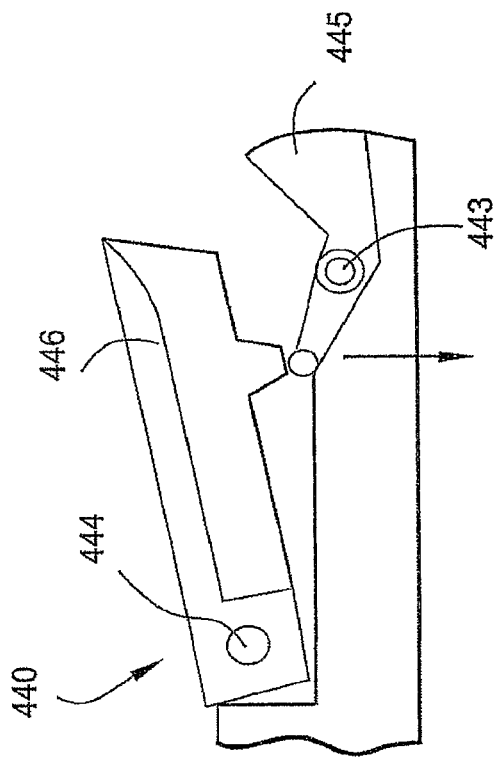
Figure 18:
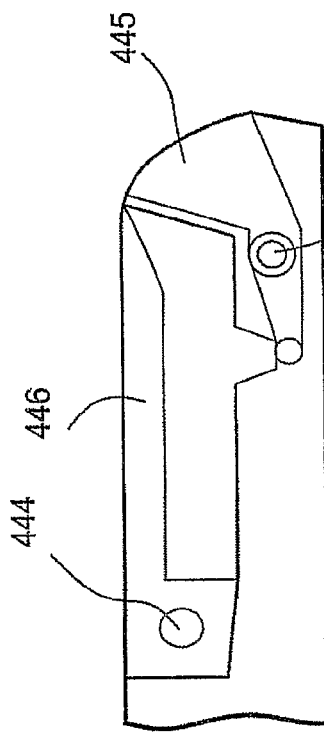

4.5 Cradle with Pivotable Front Guard and Pivotable Humidifier Retaining Portion FIGS. 17-22 illustrate a cradle 440 according to another embodiment of the present invention. In this embodiment, the cradle 440 includes two separate hinges 443, 444 that allow independent movement of a front guard 445 and a humidifier retaining portion 446, respectively. The front guard 445 is pushed or pivoted downwardly which in turn lifts the humidifier retaining portion 446 so it can pivot in an upward direction (as shown in FIGS. 17, 20, and 22). This subsequently allows easy insertion of the humidifier tub 50 into the humidifier retaining portion 446. The humidifier retaining portion 446 has edges adapted to receive sides of the humidifier tub 50 therein. Once the humidifier tub 50 is inserted within the humidifier retaining portion 446, the front guard 445 is released which allows both the front guard 445 and the humidifier retaining portion 446 to clasp the humidifier tub 50 and move the humidifier tub downwardly against the heater plate of the cradle 440 (see FIGS. 18, 19, and 21). Thus, the front guard 445 clamps the humidifier retaining portion 446 in a closed position. In an embodiment, a spring provides a bias to force the front guard 445 and the humidifier retaining portion 446 into a closed or humidifier retaining position.

4.6 Cradle with Front Guard and Pressure Pads

Figure 27:
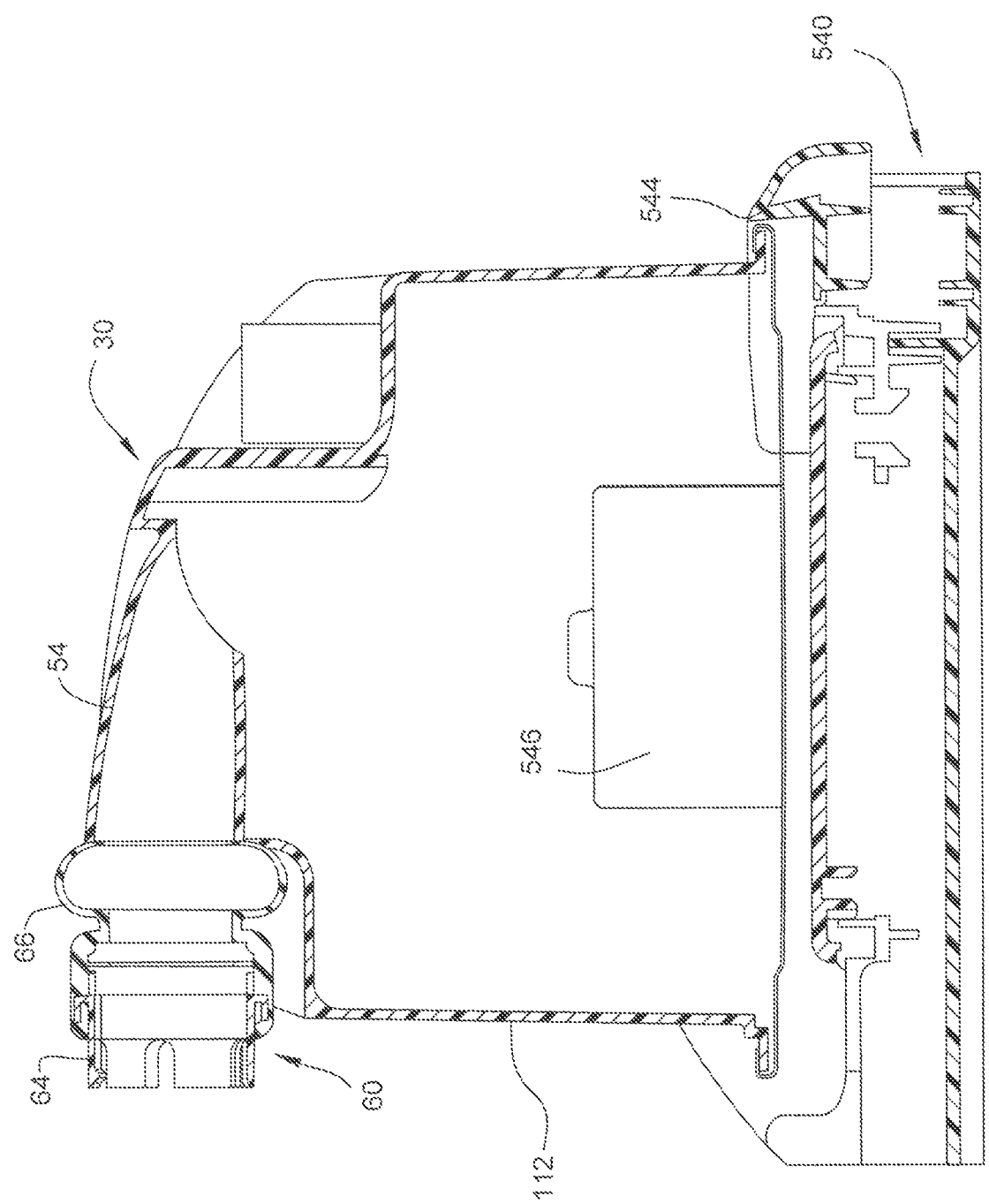
FIG. 27 is a cross-sectional view through the humidifier tub and cradle shown in FIG. 26.

FIGS. 23-27 illustrate a cradle 540 according to yet another embodiment of the present invention. In this embodiment, the cradle 540 includes a front guard or stop 544 and at least two pressure pads 546. In the illustrated embodiment, a pressure pad 546 is positioned on each side of the cradle 540 so that each pressure pad 546 is offset from a receiving side of the cradle 540 so that each side of the cradle includes a C-shaped channel adapted to slidingly receive a respective shoulder 104 of the humidifier tub 50 with the ramped portions 108 being received before the main portions 106. A spring 545 is attached to each pressure pad 546. The spring 545 is configured to force the respective pressure pad 546 in a downward direction toward the bottom of the cradle 540. The front guard or stop 544 includes a spring that forces the front guard or stop 544 upwardly to protect against access to the cradle 540 and prevent the humidifier tub 50 from falling out when installed. To install the humidifier tub 50 to the cradle 540, the front guard or stop 544 is pushed downwardly, thereby allowing the humidifier tub 50 to access the cradle 540 (see FIG. 24). The shoulders 104 of the humidifier tub 50 are then inserted underneath each of the pressure pads 546 thereby causing the pressure pads 546 to be deflected upwards against biasing of the springs 545. This allows the humidifier tub 50 to slide into the cradle 540 (see FIGS. 25-27). Once the humidifier tub 50 is located within the cradle 540, the pressure pads 546 supply the force to maintain the base of the humidifier tub 50 against the heater plate 542. In addition, once the humidifier tub 50 is fully inserted in the cradle 40, the front guard or stop 544 is moved vertically relative to the humidifier tub 50, thereby preventing withdrawal of the humidifier tub 50 in a direction opposite the installation direction (i.e., withdrawal direction). In an embodiment, movement of the front guard or stop 544 is coordinated with actuation of the pressure pads 546. Preferably, the pressure pads 546 are made of smooth material that provides low friction against the humidifier tub 50 when it is inserted into the cradle 540. FIGS. 26 and 27 illustrate the humidifier tub 50 located within the cradle 540 and the inlet 54 of the humidifier tub 50 engaged with the connector 60 shown in FIGS. 5-7.

4.7 Water Damage Mitigation

In addition to the protection afforded by the tub design, the flow generator also has one or more water damage mitigating features.

System goals: The combined system (the flow generator and humidifier) should be able to prevent water entry into the flow generator from scenarios where the unit (flow generator and humidifier) is tipped up to 60° in any direction (e.g., backwards or sidewards). Even though the flow generator and/or humidifier is ideally designed to prevent water entry into the flow generator, the flow generator should be capable of handling spill-back (e.g., about 100 ml) from the humidifier. Spill-back can occur if water is accidentally introduced directly via the outlet port. The device should not be damaged, and remain safe, with 100 ml introduced, assuming the device remains in the horizontal operating position. It should be possible to drain any such water that has entered the flow generator (contained within the Outlet Muffler/sump). Furthermore, the flow generator should satisfy the IPX1 rating requirements, and the requirements of IEC60601.1, to cope with external spillage of water by user.

Figure 28:
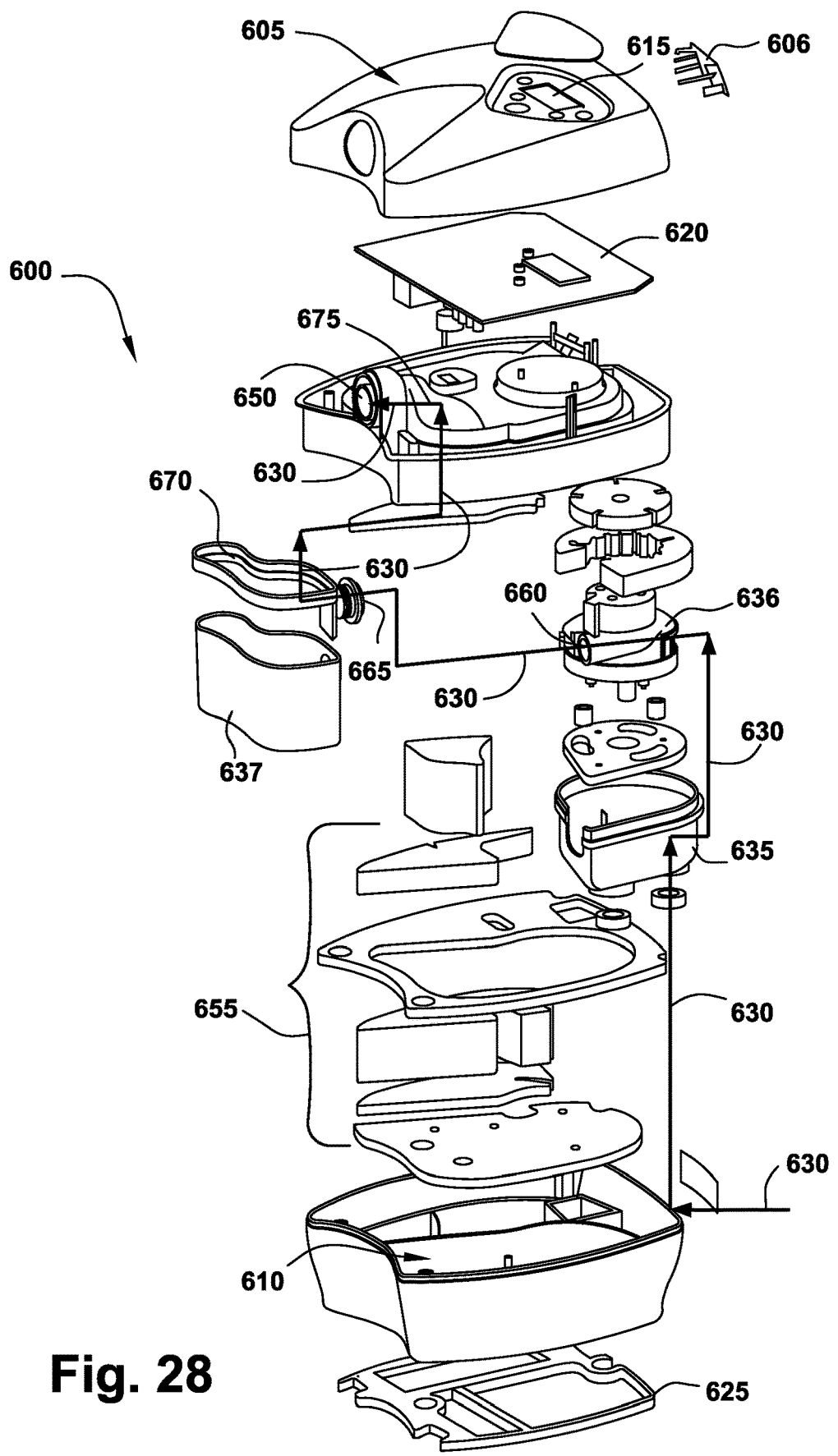
FIG. 28 is an exploded view of a flow generator according to an embodiment of the present invention.

One or more of the above goals can be achieved by implementation of the illustrative flow generator design shown in FIG. 28. FIG. 28 shows a flow generator 600 having a top case 605 and a bottom case 610. Top case 605 is provided with a keypad 615 that is operably coupled to a main PCB 620 with SMPS. Bottom case 610 is provided with base rubber feet 625. Arrows 630 schematically show the approximate path of air as it flows into, through and out of the flow generator 600. The bottom case 610 includes an inlet that directs incoming air to a motor chamber 635 that houses a motor 636. The motor 636 pressurizes the air and directs it to a muffler (or sound muffler) 637 that provides acoustic noise reduction. From the muffler 637, the pressurized gas exits via a flow generator air outlet (or flow generator air outlet port) 650 that is in communication with an air delivery conduit. Sound insulation materials 655 may be provided, but these are preferably outside the air path.

The ability to cope with water intake at the flow generator air outlet 650 is achieved in this example by having the muffler 637 act essentially as a water sump/pump, where water cannot reach the electronics or the motor unless the device is intentionally tipped over and/or tilted backwards.

Water that has entered the flow generator 600, and is contained in the muffler 637, can be drained by tilting the flow generator forward for water to exit the air delivery port. The flow generator air outlet 650 of flow generator 600 is arranged such that when the device is tipped forward it is the lowest point of the volume where water is trapped. Otherwise, the water will simply evaporate over time.

Other water mitigation features include the following features, each of which can be used alone or in combination with one or more of the other features:

Mounting the blower air inlet downwards, allowing spill back from the Humidifier to drain out of the blower inlet (into the Fan Cover) and away from the motor;

Having a very large volume (essentially the vacant space of bottom case—much larger than 100 ml) outside of and lower than the blower, so that water spill back has to completely fill this chamber before it can reach the motor;

Placing all electronics at the top of the device well away from internal water; and/or Placing the electrical interfaces (all cable connections including power) not only high on the device but above the air inlet opening where spilled water could enter the device.

For IPX1 and IEC60601.1 tests, sealing should be provided on the joints between keypad 615 and top case 605. Top case 605 shrouding 606 may also be constructed to form an "awning" over the power inlet and humidifier communications sockets. The joint between the top and bottom cases is designed to be noise tight.

The geometry of the flow generator layout is such that the sump chamber of the muffler 637 and the flow generator air outlet port 650 are not axially aligned with a motor outlet 660. As shown in FIG. 28, the motor outlet 660 directs the pressurized gas to a fitting 665 that is in communication with the chamber. The fitting 665 is formed as part of, or is otherwise provided to a gasket seal 670 that follows the contour of the chamber. While the lower portion of the seal 670 contacts the chamber, the upper portion of the seal contacts a cover member or portion 675 that may be integrally formed with the blower outlet, etc.

Figure 29:
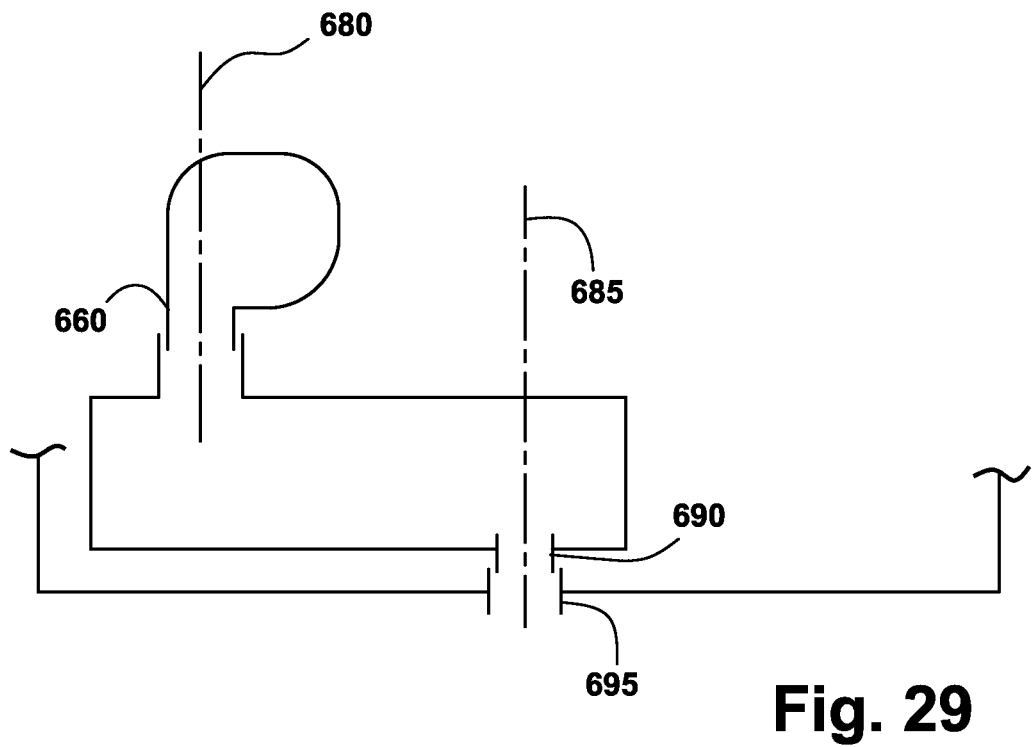
FIG. 29 is a schematic drawing illustrating the general architecture of a portion of a flow generator according to an embodiment of the present invention.

As schematically shown in FIG. 29, the axis 680 of the motor outlet 660 is offset from the axis 685 of the chamber outlet 690 and/or blower outlet 695. Thus, any water that enters the chamber from the humidifier will not be directly channeled to the motor outlet 660.

Figure 30:
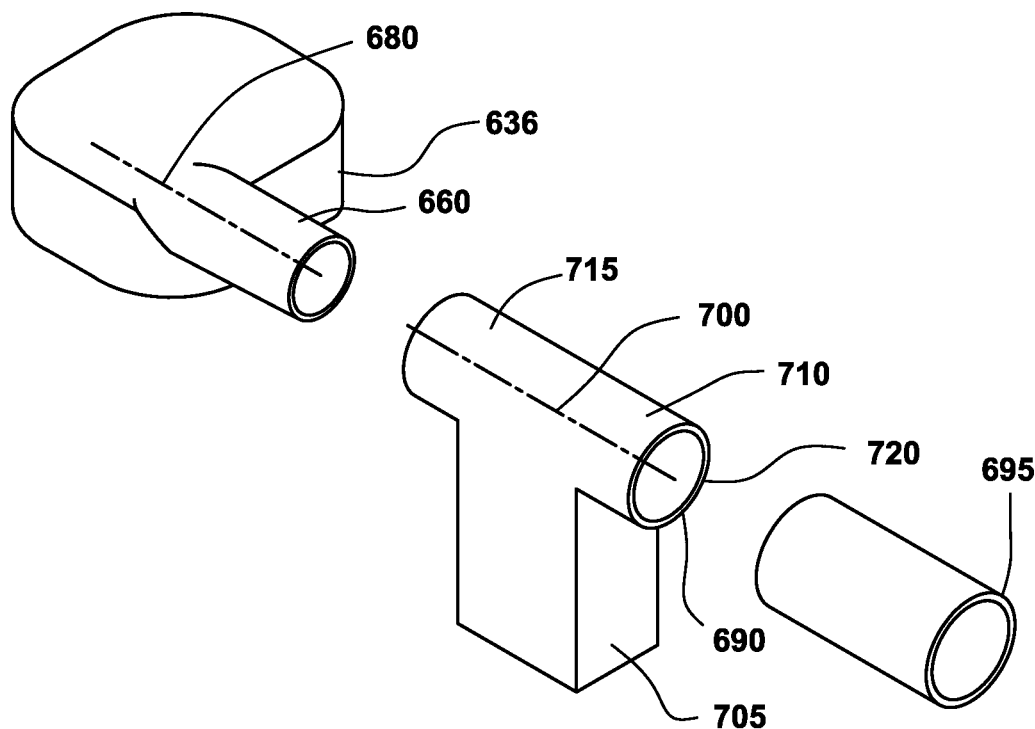
FIG. 30 is a schematic exploded view of a portion of a flow generator according to an embodiment of the present invention.

In an alternative shown in FIG. 30, the axis 680 of the motor outlet 660 can be aligned with the axis 700 of the chamber/blower outlet 690, 695, yet any water from the humidifier is not directly channeled to the motor outlet 660 because a chamber 705 is formed on a lower part of a connecting tube 710 that connects the motor outlet to the flow generator outlet. The tube has inlet and outlet portions 715, 720. The chamber 705 is provided to store a volume of water that may be accidentally introduced into the flow generator from the humidifier. This water will evaporate and/or will be reintroduced into the air path to add extra humidity, or the water can simply be emptied out by tilting or by use of a drain. The arrangement in FIG. 30 can be used in the flow generator shown in, for example, FIG. 14 of US patent application publication no. US 2005/0103339 A1, incorporated herein by reference in its entirety.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

What is claimed is:

1. A flow generator for a CPAP system configured to deliver a pressurized flow of respiratory gas to a patient's airways, the flow generator comprising:

a housing;

a motorized fan positioned within the housing, the motorized fan comprising an outlet and being configured to pressurize the flow of respiratory gas;

an outlet port in the housing that is connectable to a humidifier or an air delivery tube, the outlet port being configured so that the pressurized flow of respiratory gas is discharged from the flow generator through the outlet port;

a conduit that provides a connection between the motorized fan outlet and the outlet port, a first end of the conduit being connected to the motorized fan outlet and a second end of the conduit being connected to the outlet port; and a water collection receptacle configured to collect water from the conduit that has already entered the flow generator through the outlet port before the water reaches the motorized fan outlet.

2. The flow generator of claim 1, wherein the water collection receptacle is configured to prevent the water that has already entered the flow generator through the outlet port from reaching the motorized fan outlet when the flow generator is tilted up to 60 degrees in any direction from the operating upright orientation.

3. The flow generator of claim 1, wherein the water collection receptacle has a volume of at least 100 mL.

4. The flow generator of claim 1, wherein an inlet of the motorized fan faces downward toward a bottom portion of the housing when the flow generator is in an operating upright orientation.

5. The flow generator of claim 1, wherein the water collection receptacle is a sump chamber.

6. The flow generator of claim 1, wherein the water collection receptacle is a noise reducing muffler.

7. The flow generator of claim 1, wherein the water collection receptacle is a lower part of the conduit that provides a connection between the motorized fan outlet and the outlet port.

8. The flow generator of claim 1, wherein the outlet port and the motorized fan outlet are axially aligned with each other.

9. The flow generator of claim 1, wherein the water collection receptacle is configured to passively humidify the pressurized flow of respiratory gas.

10. The flow generator of claim 1, wherein the water collection receptacle is configured to prevent the water that has already entered the flow generator through the outlet port from reaching the motorized fan outlet when the flow generator is tilted up to 60 degrees in any direction from the operating upright orientation, wherein the water collection receptacle has a volume of at least 100 mL, wherein an inlet of the motorized fan faces downward toward a bottom portion of the housing when the flow generator is in an operating upright orientation, wherein the water collection receptacle is a sump chamber, a noise reducing muffler, and/or a lower part of the conduit that provides a connection between the motorized fan outlet and the outlet port, wherein the outlet port and the motorized fan outlet are axially aligned with each other, wherein the water collection receptacle is configured to passively humidify the pressurized flow of respiratory gas, and wherein an air outlet of the conduit is at substantially the same height as the motorized fan outlet when the flow generator is in an operating upright orientation.

11. The flow generator of claim 1, wherein an air outlet of the conduit is at substantially the same height as the motorized fan outlet when the flow generator is in an operating upright orientation.

12. The flow generator of claim 1, wherein the conduit and the water collection receptacle is located inside the housing.

13. A CPAP system configured to deliver a pressurized flow of respiratory gas to a patient's airways, the CPAP system comprising:
   the flow generator of claim 1; and
   a humidifier with an air inlet configured to removably connect to the flow generator outlet port.

14. A flow generator for a CPAP system configured to deliver a pressurized flow of respiratory gas to a patient's airways, the flow generator comprising:
   a housing;
   a motorized fan positioned within the housing, the motorized fan comprising a an outlet and being configured to pressurize the flow of respiratory gas;
   an outlet port in the housing that is connectable to a humidifier or an air delivery tube, the outlet port being configured so that the pressurized flow of respiratory gas is discharged from the flow generator through the outlet port;
   an airflow path within the housing, a portion of the airflow path extending from an outlet of the motorized fan to the outlet port; and
   a water collection receptacle comprising a portion of the airflow path that is between the motorized fan outlet and the outlet port, the water collection receptacle being configured to collect water that has already entered the flow generator through the outlet port before the water reaches the motorized fan outlet, the water collection receptacle comprising a conduit portion configured to receive the water from the outlet port and a sump chamber portion below the conduit portion that is configured to collect the water, the conduit portion being configured to convey the pressurized respiratory gas from the motorized fan outlet to the outlet port.

15. The flow generator of claim 14, wherein the water collection receptacle is configured to prevent the water that has already entered the flow generator through the outlet port from reaching the motorized fan outlet when the flow generator is tilted up to 60 degrees in any direction from the operating upright orientation.

16. The flow generator of claim 14, wherein an inlet of the motorized fan faces downward toward a bottom portion of the housing when the flow generator is in an operating upright orientation.

17. The flow generator of claim 14, wherein the water collection receptacle is a noise reducing muffler.

18. The flow generator of claim 14, wherein the outlet port and the motorized fan outlet are axially aligned with each other.

19. The flow generator of claim 14, wherein the water collection receptacle is configured to passively humidify the pressurized flow of respiratory gas.

20. The flow generator of claim 14, wherein the water collection receptacle is configured to prevent the water that has already entered the flow generator through the outlet port from reaching the motorized fan outlet when the flow generator is tilted up to 60 degrees in any direction from the operating upright orientation,
   wherein the water collection receptacle has a volume of at least 100 mL,
   wherein an inlet of the motorized fan faces downward toward a bottom portion of the housing when the flow generator is in an operating upright orientation,
   wherein the water collection receptacle is a noise reducing muffler,
   wherein the outlet port and the motorized fan outlet are axially aligned with each other,
   wherein the water collection receptacle is configured to passively humidify the pressurized flow of respiratory gas, and
   wherein an air outlet of the conduit portion of the water collection receptacle is at substantially the same height as the motorized fan outlet when the flow generator is in an operating upright orientation.

21. The flow generator of claim 14, wherein an air outlet of the conduit portion of the water collection receptacle is at substantially the same height as the motorized fan outlet when the flow generator is in an operating upright orientation.

22. The flow generator of claim 14, wherein the water collection receptacle is located inside the housing.

23. A CPAP system configured to deliver a pressurized flow of respiratory gas to a patient's airways, the CPAP system comprising:
   the flow generator of claim 14; and
   a humidifier with an air inlet configured to removably connect to the flow generator outlet port.

* * * * *